(12) United States Patent
Therriault et al.

(10) Patent No.: US 10,647,057 B2
(45) Date of Patent: May 12, 2020

(54) ELECTRICALLY CONDUCTIVE INK FOR SOLVENT-CAST 3D PRINTING

(71) Applicant: POLYVALOR, LIMITED PARTNERSHIP, Montreal (CA)

(72) Inventors: Daniel Therriault, St-Laurent (CA); Kambiz Chizari, Montreal (CA)

(73) Assignee: POLYVALOR, LIMITED PARTNERSHIP (CA)

(*) Notice: Subject to any disclaimer, the term of this patent is extended or adjusted under 35 U.S.C. 154(b) by 112 days.

(21) Appl. No.: 15/654,094

(22) Filed: Jul. 19, 2017

(65) Prior Publication Data

US 2018/0022023 A1 Jan. 25, 2018

Related U.S. Application Data

(60) Provisional application No. 62/364,467, filed on Jul. 20, 2016.

(51) Int. Cl.
*B29C 64/153* (2017.01)
*B33Y 10/00* (2015.01)
(Continued)

(52) U.S. Cl.
CPC .......... *B29C 64/153* (2017.08); *B29C 64/106* (2017.08); *B33Y 10/00* (2014.12); *B33Y 70/00* (2014.12); *C07C 19/03* (2013.01); *C07C 31/02* (2013.01); *C07C 307/08* (2013.01); *C08B 37/003* (2013.01); *C08J 3/075* (2013.01);
(Continued)

(58) Field of Classification Search
CPC .......... B32Y 10/00; B32Y 70/00; C09D 5/24; C08K 3/041
See application file for complete search history.

(56) References Cited

U.S. PATENT DOCUMENTS

| 4,938,816 A | 7/1990 | Beaman et al. |
| 5,121,329 A | 6/1992 | Crump |

(Continued)

FOREIGN PATENT DOCUMENTS

| CN | 101413154 B | 4/2009 |
| CN | 102229743 A | 11/2011 |

(Continued)

OTHER PUBLICATIONS

Guo et al., Nanoscale, 2015, 7, 6451-6456.*
(Continued)

*Primary Examiner* — Vu A Nguyen
(74) *Attorney, Agent, or Firm* — Lavery, De Billy, LLP; Isabelle Pelletier

(57) ABSTRACT

An ink for solvent-cast 3D printing is provided. The ink comprises a solution or gel of a polymer in a volatile solvent, and carbon nanotubes dispersed in the solution or gel. In the ink, the carbon nanotubes are present in a carbon nanotubes:polymer weight ratio between about 20:80 and about 40:60, and the polymer and carbon nanotubes total concentration is between about 20 and about 35 wt %, based on the total weight of the ink. There is also provided a 3D printer ink cartridge comprising the ink; a method of manufacturing the ink; a method of manufacturing a solvent-cast 3D printed material using the ink, a solvent-cast 3D printed material as well as uses thereof.

19 Claims, 22 Drawing Sheets

(51) Int. Cl.

| | |
|---|---|
| B33Y 70/00 | (2020.01) |
| C09D 5/24 | (2006.01) |
| C08K 3/04 | (2006.01) |
| C08B 37/08 | (2006.01) |
| C07C 19/03 | (2006.01) |
| C07C 307/08 | (2006.01) |
| C07C 31/02 | (2006.01) |
| C08J 3/075 | (2006.01) |
| B29C 64/106 | (2017.01) |
| C09D 7/40 | (2018.01) |
| C09D 7/61 | (2018.01) |
| C09D 105/08 | (2006.01) |

(52) U.S. Cl.
CPC ............... *C09D 5/24* (2013.01); *C09D 7/61* (2018.01); *C09D 7/70* (2018.01); *C09D 105/08* (2013.01); *B29K 2995/0005* (2013.01)

(56) References Cited

U.S. PATENT DOCUMENTS

| | | | |
|---|---|---|---|
| 2006/0078705 | A1 | 4/2006 | Glatkowski et al. |
| 2015/0366073 | A1 | 12/2015 | Magdassi et al. |

FOREIGN PATENT DOCUMENTS

| | | |
|---|---|---|
| CN | 102952383 B | 3/2013 |
| CN | 103665799 A | 3/2014 |
| CN | 104752530 A | 7/2015 |
| WO | 2014118783 A1 | 8/2014 |

OTHER PUBLICATIONS

Postiglione et al., Composites Part A: Applied Science and Manufacturing, vol. 76, Sep. 2015, pp. 110-114.*

Lu et al., Adv. Mater. 2010, 22, 3745-3748.*

Agarwala, M.; Bourell, D.; Beaman, J.; Marcus, H.; Barlow, J., "Direct selective laser sintering of metals", Rapid Prototyping Journal 1995, 1, 26.

Aldrich Materials Science, Material Matters, vol. 11, No. 2, Jul. 2016.

An, K. H.; Jeong, S. Y.; Hwang, H. R.; Lee, Y. H., "Enhanced Sensitivity of a Gas Sensor Incorporating Single-Walled Carbon Nanotube-Polypyrrole Nanocomposites", Advanced Materials 2004, 16, 1005.

Arjmand, M.; Mahmoodi, M.; Gelves, G. A.; Park, S.; Sundararaj, U., "Electrical and electromagnetic interference shielding properties of flow-induced oriented carbon nanotubes in polycarbonate", Carbon 2011, 49, 3430.

Bae, S.; Kim, H.; Lee, Y.; Xu, X.; Park, J.-S.; Zheng, Y.; Balakrishnan, J.; Lei, T.; Kim, H. R.; Song, Y. I.; Kim, Y.-J.; Kim, K. S.; Ozyilmaz, B.; Ahn, J.-H.; Hong, B. H.; Iijima, S., "Roll-to-roll production of 30-inch graphene films for transparent electrodes", Nat Nano 2010, 5, 574.

Baughman, R. H.; Zakhidov, A. A.; De Heer, W. A., "Carbon Nanotubes—The Route Toward Applications", Science 2002, 297, 787.

Chen, C.; Yang, C.; Li, S.; Li, D., "A three-dimensionally chitin nanofiber/carbon nanotube hydrogel network for foldable conductive paper", Carbohydrate polymers 2015, 134, 309.

Chizari, K.; Therriault, D., "Conductive Filaments from CNTs/PLA Composites", Poster presented at the ASME 2014 International Mechanical Engineering Congress and Exposition, Nov. 14-20, 2014, Montreal, Canada.

Chizari, K.; Therriault, D., "Fabrication of Conductive Microfilaments and Liquid Sensor from CNTs/PLA" in Design, Manufacturing and Applications of Composites Tenth Workshop 2014: Proceedings of the Tenth Joint Canada-Japan Workshop on Composites, Destech Publications Inc., 2015, pp. 214-221 (proceeding of a conference held in Aug. 2014 in Vancouver, Canada).

Chizari, K.; Therriault, D., "Fabrication of Conductive Microfilaments and Liquid Sensor from CNTs/PLA", Conference presented at the Tenth Joint Canada-Japan Workshop on Composites, Aug. 2014, Vancouver, Canada.

Czyzewski, J.; Burzynski, P.; Gawel, K.; Meisner,J., "Rapid prototyping of electrically conductive components using 3D printing technology", Journal of Materials Processing Technology 2009, 209, 5281.

Eda, G.; Chhowalla, M., "Graphene-based Composite Thin Films for Electronics", Nano Letters 2009, 9, 814.

Farahani, R. D.; Chizari, K; Therriault, D., "Three-dimensional printing of helical microstructures: A review", Nanoscale, 2014, 6, 10470.

Farahani, R. D.; Dalir, H.; Le Borgne, V.; Gautier, L. A.; El Khakani, M. A.; Levesque, M.; Therriault, D., "Direct-write fabrication of freestanding nanocomposite strain sensor", Nanotechnology 2012, 23, 085502.

Farahani, R. D.; Lebel, L; Therriault, D., "Processing parameters investigation for the fabrication of self-supported and freeform polymeric microstructures using ultraviolet-assisted three-dimensional printing", Journal of Micromechanics and Microengineering 2014, 24, 055020.

Farahani, R.D.; Dube, M.; Therriault, D., "Three-Dimensional Printing of Multifunctional Nanocomposites: Manufacturing Techniques and Applications", Advanced Materials 2016, 28, 5794.

Gagne, M.; Therriault, D., "Lightning strike protection of composites", Progress in Aerospace Sciences 2014, 64, 1.

Guo, S.-Z.; Gosselin, F.; Guerin, N.; Lanouette, A.-M.; Heuzey, M.-C.; Therriault, D., "Solvent-Cast Three-Dimensional Printing of Multifunctional Microsystems", Small 2013, 9, 4118.

Guo, S.-Z.; Heuzey, M.-C.; Therriault, D., "Properties of Polylactide Inks for Solvent-Cast Printing of Three-Dimensional Freeform Microstructures", Langmuir 2014, 30, 1142.

Guo, S.-Z.; Yang, X.; Heuzey, M.-C.; Therriault, D., "3D printing of a multifunctional nanocomposite helical liquid sensor", Nanoscale 2015, 7, 6451.

Hu, N.; Karube, Y.; Arai, M.; Watanabe, T.; Yan, C.; Li, Y.; Liu, Y.; Fukunaga, H., "Investigation on sensitivity of a polymer carbon nanotube composite strain sensor", Carbon 2010, 48, 680.

Hu, Y.; Chen, W.; Lu, L.; Liu, J.; Chang, C., "Electromechanical actuation with controllable motion based on a single-walled carbon nanotube and natural biopolymer composite", ACS nano 2010, 4, 3498.

Hutmacher, D. W., "Scaffolds in tissue engineering bone and cartilage", Biomaterials 2000, 21, 2529.

Kang, I.; Schulz, M. J.; Kim, J. H.; Shanov, V.; Shi, D., "A carbon nanotube strain sensor for structural health monitoring", Smart Materials and Structures 2006, 15, 737.

Kang, X.; Mai, Z.; Zou, X.; Cai, P.; Mo, J., "A sensitive nonenzymatic glucose sensor in alkaline media with a copper nanocluster/ multiwall carbon nanotube-modified glassy carbon electrode", Analytical Biochemistry 2007, 363, 143.

Kobashi, K; Villmow, T.; Andres, T.; Haussler, L; Potschke, P., "Investigation of liquid sensing mechanism of poly(lactic acid)/ multi-walled carbon nanotube composite films", Smart Materials and Structures 2009, 18, 035008.

Kobashi, K; Villmow, T.; Andres, T.; Potschke, P., "Liquid sensing of melt-processed poly(lactic acid)/multi-walled carbon nanotube composite films", Sensors and Actuators B: Chemical 2008, 134, 787.

Ladd C.; So,J.-H.; Muth, J.; Dickey, M. D., "3D Printing of Free Standing Liquid Metal Microstructures", Advanced Materials 2013, 25, 5081.

Lebel, L. L.; Aissa, B.; El Khakani, M. A.; Therriault, D., "Ultraviolet-Assisted Direct-Write Fabrication of Carbon Nanotube/Polymer Nanocomposite Microcoils", Advanced Materials 2010, 22, 592.

Leigh, S. J.; Bradley, R. J.; Purssell, C. P.; Billson, D. R.; Hutchins, D. A.,"A Simple, Low-Cost Conductive Composite Material for 3D Printing of Electronic Sensors", Plos one 2012, 7, e49365.

Li, N.; Huang, Y.; Du, F.; He, X.; Lin, X.; Gao, H.; Ma, Y.; Li, F.; Chen, Y.; Eklund, P. C., "Electromagnetic interference (EMI) shielding of single-walled carbon nanotube epoxy composites", Nano Letters 2006, 6, 1141.

(56) References Cited

OTHER PUBLICATIONS

Lipomi, D. J.; Vosgueritchian, M.; Tee, B. C.-K.; Hellstrom, S. L.; Lee, J. A.; Fox, C. H.; Bao, Z, "Skin-like pressure and strain sensors based on transparent elastic films of carbon nanotubes", Nat Nano 2011, 6, 788.

Lu, L.; Chen, W., "Biocompatible composite actuator: a supramolecular structure consisting of the biopolymer chitosan, carbon nanotubes, and an ionic liquid", Advanced Materials 2010, 22, 3745.

Ong, K. G.; Zeng, K; Grimes, C. A., "A Wireless, Passive Carbon Nanotube-Based Gas Sensor", IEEE Sensors Journal, 2002, 2, 82.

Pham, D. T.; Gault, R. S., "A comparison of rapid prototyping technologies", International Journal of Machine Tools and Manufacture 1998, 38, 1257.

Postiglione, G.; Natale, G.; Griffini, G.; Levi, M.; Turri, S., "Conductive 3D microstructures by direct 3D printing of polymer/carbon nanotube nanocomposites via liquid deposition modeling", Composites Part A: Applied Science and Manufacturing 2015, 76, 110.

Qin, Z.; Compton, B. G.; Lewis, J. A.; Buehler, M. J., "Structural optimization of 3D-printed synthetic spider webs for high strength", Nat Commun 2015, 6.

Rogers, J. A.; Someya, T.; Huang, Y., "Materials and Mechanics for Stretchable Electronics", Science 2010, 327, 1603.

Stankovich, S.; Dikin, D. A.; Dommett, G. H. B.; Kohlhaas, K. M.; Zimney, E. J.; Stach, E. A.; Piner, R. D.; Nguyen, S. T.; Ruoff, R. S., "Graphene-based composite materials", Nature 2006, 442, 282.

Thostenson, E. T.; Chou, T.-W., "Carbon Nanotube Networks: Sensing of Distributed Strain and Damage for Life Prediction and Self Healing", Advanced Materials 2006, 18, 2837.

Villmow, T.; Pegel, S.; John, A.; Rentenberger, R.; Potschke, P., "Liquid sensing: smart polymer/CNT composites", Materials Today 2011, 14, 340.

Wang, J., "Carbon-Nanotube Based Electrochemical Biosensors: A Review" Electroanalysis 2005, 17, 1.

Wang, J.; Musameh, M., "Carbon Nanotube/Teflon Composite Electrochemical Sensors and Biosensors", Analytical Chemistry 2003, 75, 2075.

Yamada, T.; Hayamizu, Y.; Yamamoto, Y.; Yomogida, Y.; Izadi-Najafabadi, A.; Futaba, D. N.; Hata, K., "A stretchable carbon nanotube strain sensor for human-motion detection", Nat Nano 2011, 6, 296.

Zhang, X.; Jiang, X. N.; Sun, C., "Micro-stereolithography of polymeric and ceramic microstructures", Sensors and Actuators A: Physical 1999, 77, 149.

Zhao H.; Shen, J.; Zhang, J.; Wang, H.; Wilkinson, D. P.; Gu,C. E., "Liquid methanol concentration sensors for direct methanol fuel cells", Journal of Power Sources 2006, 159, 626.

Zhu, C.; Han, T. Y.-J.; Duoss, E.; B.; Golobic, A. M.; Kuntz, J. D.; Spadaccini, C. M.; Worsley, M. A., "Highly compressible 3D periodic graphene aerogel microlattices", Nature communications 2015, 6.

\* cited by examiner

A)

B)

A)

B)

A)

B)

ELECTRICALLY CONDUCTIVE INK FOR SOLVENT-CAST 3D PRINTING

CROSS REFERENCE TO RELATED APPLICATIONS

This application claims benefit, under 35 U.S.C. § 119(e), of U.S. provisional application Ser. No. 62/364,467, filed on Jul. 20, 2016.

FIELD OF THE INVENTION

The present invention relates to an ink for 3D printing. More specifically, the present invention is concerned with an electrically conductive ink for solvent-cast 3D printing.

BACKGROUND OF THE INVENTION 3D printing (3DP) methods build structures from a digitally designed 3D model. 3DP enables manufacturing structures with configurations with different structural parameters without the need to make a mold for each structure. This feature of 3DP make this method one of the most promising fabrication methods suitable for topology optimization.

Many different types of 3D printing methods (e.g., fused deposition modeling (FDM), selective laser sintering (SLS), stereolithography, solvent cast 3DP (SC3DP) and UV assisted 3DP (UV3DP)) have been developed so far. 3D printing of conductive materials has always been a challenge because the most frequently used conductive materials are metals. Due to their high melting temperature, their utilization as an ink for 3DP methods involving melting and extruding the material from a nozzle (i.e., FDM) is challenging. M. D. Dickey and his co-workers have reported direct-write 3D printing of metallic structures by extrusion of liquid metal from a nozzle. SLS has been used for fabrication of metallic structures by sintering of metal powder using heating originated from a laser beam. Other efforts have been done on printing of conductive polymer based nanocomposite inks using FDM, SC3DP and UV3DP. Conductive structures with electrical conductivity of ~10 S/m were made by FDM method using a carbon black/polycaprolactone composite ink. Since SC3DP and UV3DP can function at room temperature, they are not subject to the problems caused by the variations in melting point and viscosity due to the addition of fillers. Scaffolds from a graphene-based material with an electrical conductivity of 278 S/m were fabricated using a 3D printing method suitable for printing of aerogels.

Printing of conductive nanocomposites with electrical conductivity of ~100 S/m was reported for carbon nanotube (CNT)/polylactic acid (PLA) inks. However, increasing the concentration of CNT in such composites to more than 10 wt. % is challenging due to mixing difficulties. The high viscosity of the mixing materials and difficulties related to the dispersion of CNTs at high concentrations in a solvent hinders extrusion and solution mixing, respectively. On the other hand, the fabrication of highly conductive ink from polymer-based composite inks is highly demanding and hardly accessible due to extrusion difficulties of highly doped nanocomposite inks from fine nozzles. Composite inks with high concentrations of conductive fillers have different viscosity behavior which blocks the printing nozzle in 3D printing methods involving melting and extruding an ink, such as fusion deposition modeling (FDM), which is the most popular 3D printing method.

SUMMARY OF THE INVENTION

In accordance with the present invention, there is provided:

1. An ink for solvent-cast 3D printing, the ink comprising: a solution or a gel of a polymer in a volatile solvent, and carbon nanotubes dispersed in the solution or gel,
   wherein the carbon nanotubes are present in a carbon nanotubes:polymer weight ratio between about 20:80 and about 40:60, and
   wherein the polymer and carbon nanotubes total concentration is between about 20 and about 35 wt %, based on the total weight of the ink.
2. The ink of item 1, wherein the carbon nanotubes:polymer weight ratio is:
   about 20:80, about 25:75, about 30:70, or about 35:65 or more and/or
   about 40:60, about 35:65, about 30:70, or about 25:75 or less
3. The ink of item 1 or 2, wherein the carbon nanotubes: polymer weight ratio is between about 20:80 and about 35:65, more preferably between about 20:80 and about 30:70, yet more preferably between about 20:80 and about 25:75, and most preferably is about 20:80, about 25:75, about 30:70, or about 35:65.
4. The ink of any one of items 1 to 3, wherein the polymer and carbon nanotubes total concentration is:
   about 20 wt %, about 21 wt %, about 22 wt %, about 23 wt %, about 24 wt %, about 25 wt %, about 26 wt %, about 27 wt %, about 28 wt %, about 29 wt %, or about 30 wt % or more and/or
   about 35 wt %, about 34 wt %, about 33 wt %, about 32 wt %, about 31 wt %, about 30 wt %, about 29 wt %, about 28 wt %, about 27 wt %, about 26 wt %, or about 25 wt % or less,
   based on the total weight of the ink.
5. The ink of any one of items 1 to 4, wherein the polymer and carbon nanotubes total concentration is between about 25 and about 30 wt %, based on the total weight of the ink.
6. The ink of any one of items 1 to 5, wherein the carbon nanotubes are single-wall carbon nanotubes or multiwall carbon nanotubes, preferably multiwall carbon nanotubes, such as those sold under the tradename Nanocyl™ NC7000.
7. The ink of any one of items 1 to 6, wherein the polymer is poly(lactic acid), polystyrene, poly(methyl acrylate), poly(methyl methacrylate), poly(n-butyl acrylate), poly(2-hydroxyethyl methacrylate), poly(glycidyl methacrylate), poly(acrylic acid), poly(N—N-dimethylacrylamide), poly(1-vinyl anthracene), poly(2-vinyl pyridine), poly(4-vinyl pyridine), poly(N-vinyl carbazole), poly(N-vinyl carbazole), poly(N-vinyl imidazole), poly(vinyl benzyl chloride), poly(4-vinyl benzoic acid), poly(vinyl acetate), polycaprolactone, poly(11-[4-(4-butylphenylazo)phenoxy]-undecyl methacrylate) (poly(AzoMA)), poly(ferrocenyldimethylsilane), polyisoprene, polybutadiene, polyisobutylene, poly propylene glycol, poly(ethylene glycol), a polysaccharide, such as chitosan, or a mixture thereof.
8. The ink of any one of items 1 to 7, wherein the solvent is dichloromethane (DCM), chloroform (CHCl$_3$), tetrahydrofuran (THF), acetone, methanol (MeOH), ethanol (EtOH), or water.
9. The ink of any one of items 1 to 8, wherein the polymer is poly(lactic acid), such as that sold under number PLA 4032D by Natureworks LLC.

10. The ink of any one of items 1 to 9, wherein the solvent is dichloromethane, chloroform, tetrahydrofuran, acetone, methanol, or ethanol, preferably dichloromethane.
11. The ink of any one of items 1 to 8, wherein the polymer is a polysaccharide, preferably chitosan.
12. The ink of any one of items 1 to 8 and 11, wherein the solvent is water.
13. The ink of any one of items 1 to 12, wherein the ink further comprises one or more additive.
14. The ink of any one of items 1 to 13, wherein the ink further comprises one or more weak organic acid, preferably 70 vol % acetic acid alone or together with 10 vol % lactic acid and 3 wt % citric acid, the vol % being based on the total volume of the solvent and acids and the wt % being based on the total weight of the solvent and acids.
15. The ink of any one of items 1 to 14, wherein the solution or gel of the polymer in the volatile solvent is a solution of poly(lactic acid) in dichloromethane.
16. The ink of any one of items 1 to 14, wherein the solution or gel of the polymer in the volatile solvent is a chitosan hydrogel.
17. The ink of claim 16, wherein the chitosan hydrogel comprises or more weak organic acid, preferably 70 vol % acetic acid alone or together with 10 vol % lactic acid and 3 wt % citric acid, the vol % being based on the total volume of the water and acids and the wt % being based on the total weight of the water and acids.
18. A 3D printer ink cartridge, the cartridge comprising a container having an ink outlet, the container comprising the ink of any one of items 1 to 17.
19. The cartridge of item 18, wherein the cartridge is adapted to be installed on a 3D printer.
20. The cartridge of item 18 or 19, wherein the cartridge is adapted to be fitted to a needle for delivering the ink, so that, for ink dispensing, the ink is extruded through the ink outlet and through the needle.
21. The cartridge of any one of items 18 to 20, wherein the cartridge is designed so that when a pressure is applied by a 3D printer, the ink is extruded through the ink outlet.
22. A method of manufacturing the solvent-cast 3D printing ink of any one of items 1 to 17, the method comprising the steps of:
    a) providing a solution or a gel of a polymer in a solvent,
    b) providing carbon nanotubes in a carbon nanotubes:polymer weight ratio of between about 20:80 and about 40:60,
    c) dispersing the carbon nanotubes in the solution or gel of the polymer by ball milling, thereby producing the ink, and
    d) avoid drying the ink, thus keeping the solvent in the ink, until the ink is used for solvent-cast 3D printing.
23. The method of item 22, wherein step a) comprises mixing the polymer in the solvent until the polymer is dissolved.
24. The method of item 22 or 23, wherein the concentration of the polymer in the solution or gel of step a) is:
    about 2 wt %, about 3 wt %, about 4 wt %, about 5 wt %, about 6 wt %, about 7 wt %, about 8 wt %, about 9 wt %, or about 10 wt % or more and/or about 15 wt %, about 14 wt %, about 13 wt %, about 12 wt %, about 11 wt %, or about 10 wt % or less, based on the total weight of the solution or gel.
25. The method of any one of items 22 to 24, wherein the polymer is poly(lactic acid) and the concentration of the polymer in the solution or gel of step a) is about 10 wt %, based on the total weight of the solution or gel.
26. The method of any one of items 22 to 24, wherein the polymer is chitosan and the concentration of the polymer in the solution or gel of step a) is about 4 wt %, based on the total weight of the solution or gel.
27. The method of any one of items 22 to 26, wherein the ball milling in step c) is carried out for 10 to 30 minutes, preferably 30 minutes.
28. The method of any one of items 22 to 27, further comprising, before or after step d), the step of adding solvent, or removing part of the solvent so that the polymer and carbon nanotubes total concentration in the ink is between about 20 and about 35 wt %, based on the total weight of the ink.
29. The method of any one of items 22 to 28, further comprising the step of adding one or more additives to the solvent, to the solution or gel of the polymer, or to the ink.
30. The method of any one of items 22 to 29, further comprising the step of packaging the ink in a 3D printer ink cartridge.
31. A method of using the solvent-cast 3D printing ink any one of items 1 to 17 for manufacturing a solvent-cast 3D printed material, the method comprising the steps of:
    a) providing the solvent-cast 3D printing ink any one of items 1 to 17;
    b) using a 3D printer, extruding the ink through a needle into a controlled pattern; and
    c) allowing solvent evaporation, thereby providing the solvent-cast 3D printed material.
32. The method of item 31, wherein step a) comprises the method of manufacturing the solvent-cast 3D printing ink of any one of items 22 to 30.
33. A solvent-cast 3D printed material shaped into a controlled pattern made of a composite comprising a polymer and carbon nanotubes dispersed in a matrix of the polymer, the carbon nanotubes being present in a carbon nanotubes:polymer weight ratio between about 20:80 and about 40:60.
34. The material of item 33, manufactured by solvent-cast 3D printing of the ink of any one of items 1 to 11.
35. The material of item 33 or 34, manufactured using the method of manufacturing a solvent-cast 3D printed material of item 31 or 32.
36. The material of any one of items 33 to 35 for use as a liquid sensor.
37. A liquid sensor comprising the material of any one of items 33 to 35.
38. Use of the material of any one of items 33 to 35 as a liquid sensor.
39. The material of any one of items 33 to 35 for use as an electromagnetic interference (EMI) shield.
40. An electromagnetic interference (EMI) shield comprising the material of any one of items 33 to 35.
41. Use of the material of any one of items 33 to 35 as an electromagnetic interference (EMI) shield

DETAILED DESCRIPTION OF THE INVENTION

Figure 1:
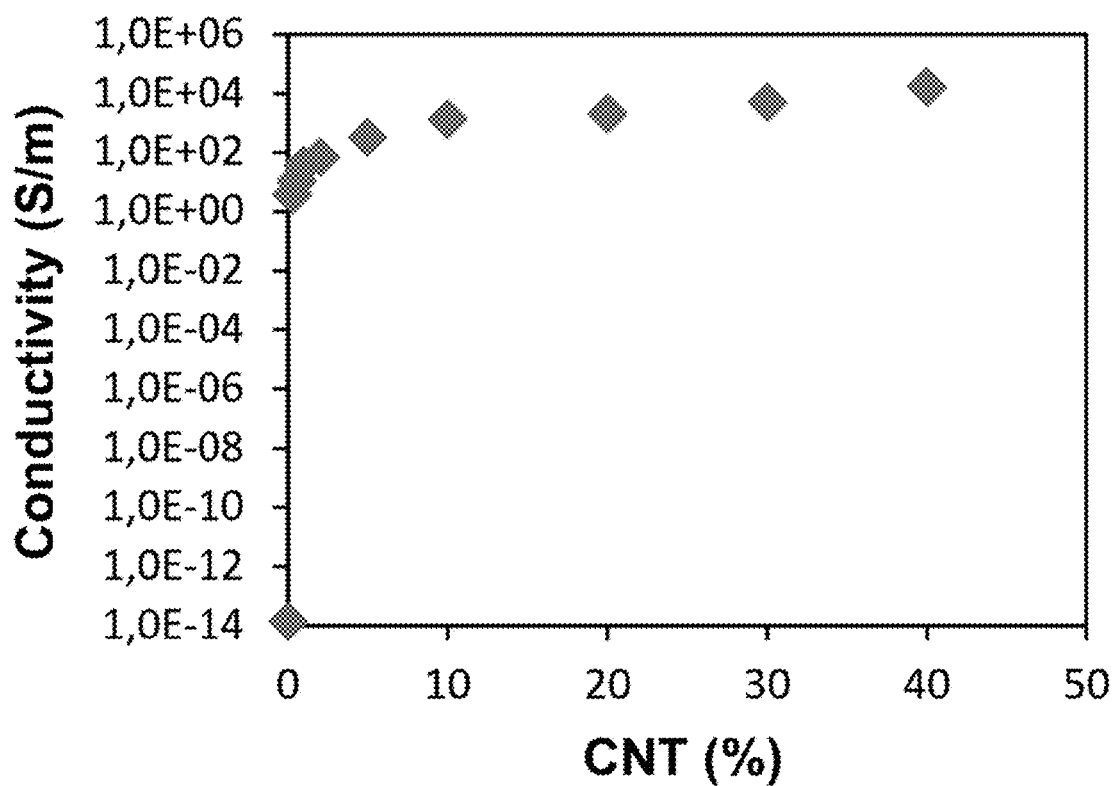
FIG. 1 shows the electrical conductivity of CNT/PLA nanocomposites as a function of CNT concentration.

The present invention relates to solvent-cast 3D printing.

In solvent-cast 3D printing, an ink containing a volatile solvent is deposited in a controlled pattern using a 3D printer. A 3D printer is a computer-controlled robot that is able to create a 3D object, usually from a model designed by a computer aided design (CAD), by laying down successive thin layers of a 3D printing ink. To make a solvent-cast 3D printed structure, the ink is extruded through a moving needle, thereby depositing the ink in the desired pattern. Usually, this pattern is multilayered. After extrusion, the solvent from the ink usually quickly evaporates (generally at room temperature) producing a solid 3D printed structure.

Ink for Solvent-Cast 3D Printing

Turning now to the invention in more details, there is provided an ink for solvent-cast 3D printing, the ink comprising:

a solution or a gel of a polymer in a volatile solvent, and
carbon nanotubes dispersed in the solution or gel, wherein the carbon nanotubes are present in a carbon nanotubes:polymer weight ratio between about 20:80 and about 40:60, and wherein the polymer and carbon nanotubes total concentration is between about 20 and about 35 wt %, based on the total weight of the ink.

Herein, an "ink for solvent-cast 3D printing" is an ink that is useful for manufacturing a 3D printed material by solvent-cast 3D-printing.

As noted above, the ink comprises the carbon nanotubes and the polymer in a certain weight ratio range. For certainty, this weight ratio is expressed as follows: weight ratio=weight of carbon nanotubes: weight of polymer. A ratio of 20:80 thus means that the ink comprises 20 wt % of carbon nanotube and 80 wt % of polymer, both percentages being based of the total weight of the polymer and nanotubes (i.e. excluding the weight of the solvent and any other potential additives).

In embodiments, the carbon nanotubes are present in a carbon nanotubes:polymer weight ratio of:
  about 20:80, about 25:75, about 30:70, or about 35:65 or more and/or
  about 40:60, about 35:65, about 30:70, or about 25:75 or less.

In preferred embodiments, the carbon nanotubes are present in a carbon nanotubes:polymer weight ratio between about 20:80 to about 35:65, more preferably between about 20:80 to about 30:70, yet more preferably between about 20:80 to about 25:75, and most preferably in a ratio of about 20:80, about 25:75, about 30:70, or about 35:65. Higher ratios were found to increase the conductivity of the ink. A ratio of about 40:60 or less ensures that the carbon nanotubes are dispersed in a matrix of the polymer. In fact, when the carbon nanotubes are present in a carbon nanotubes:polymer weight ratio higher than about 40:60, 3D printing may be difficult because the ink is then difficult to extrude through a needle. This is probably due to the presence of agglomerates forming as a result of incomplete dispersion of CNTs.

The ink is also characterized by its polymer and carbon nanotubes total concentration. For certainty, this concentration is calculated as follows:

$$\text{polymer and carbon nanotubes total concentration} = \frac{\text{weight polymer} + \text{weight carbon nanotubes}}{\text{total weight of the ink}} \times 100.$$

As stated above, the polymer and carbon nanotubes total concentration is between about 20 and about 35 wt %, based on the total weight of the ink. Higher concentrations make the ink too thick for extrusion through the needle of a 3D printer. Lower concentrations make the ink too runny for multilayer printing. In embodiments, the ink comprises the polymer and the carbon nanotubes in a total concentration of:
  about 20 wt %, about 21 wt %, about 22 wt %, about 23 wt %, about 24 wt %, about 25 wt %, about 26 wt %, about 27 wt %, about 28 wt %, about 29 wt %, or about 30 wt % or more and/or
  about 35 wt %, about 34 wt %, about 33 wt %, about 32 wt %, about 31 wt %, about 30 wt %, about 29 wt %, about 28 wt %, about 27 wt %, about 26 wt %, or about 25 wt % or less,
based on the total weight of the ink. In preferred embodiments, ink comprises the polymer and the carbon nanotubes in a total concentration between about 25 and about 30 wt %, based on the total weight of the ink.

The carbon nanotubes may be formed by any known technique and can be obtained in a variety of forms, such as, for example, soot, powder, fibers, and mixtures thereof. The carbon nanotubes may be any length, diameter, or chirality as produced by any of the various production methods. Carbon nanotubes may include, but are not limited to, single-wall carbon nanotubes (SWNTs), double-wall carbon nanotubes (DWNTs), multi-wall carbon nanotubes (MWNTs), shortened carbon nanotubes, oxidized carbon nanotubes, functionalized carbon nanotubes, unfunctionalized (pristine) carbon nanotubes, metallic nanotubes, semiconductor nanotubes, purified carbon nanotubes, metalized carbon nanotubes and combinations thereof. In preferred embodiments, the carbon nanotubes are single-wall carbon nanotubes and multiwall carbon nanotubes, more preferably multiwall carbon nanotubes, for example those sold under the tradename Nanocyl™ NC7000. In embodiment, the nanotubes may metallic nanotubes or semi-conductor nanotubes provided as a mixture or separately, depending to the end use and desired properties of the ink.

The polymer is a polymer that is soluble or that forms a gel, preferably at room temperature, in the solvent. In embodiments, the polymer is poly(lactic acid), polystyrene, poly(methyl acrylate), poly(methyl methacrylate), poly(n-butyl acrylate), poly(2-hydroxyethyl methacrylate), poly (glycidyl methacrylate), poly(acrylic acid), poly(N—N-dimethylacrylamide), poly(l-vinyl anthracene), poly(2-vinyl pyridine), poly(4-vinyl pyridine), poly(N-vinyl carbazole), poly(N-vinyl carbazole), poly(N-vinyl imidazole), poly(vinyl benzyl chloride), poly(4-vinyl benzoic acid), poly(vinyl acetate), polycaprolactone, poly(11-[4-(4-butylphenylazo) phenoxy]-undecyl methacrylate) (poly(AzoMA)), poly(ferrocenyldimethylsilane), polyisoprene, polybutadiene, polyisobutylene, poly propylene glycol, poly(ethylene glycol), or a polysaccharide, such as chitosan, or a mixture thereof.

Polysaccharides, and in particular chitosan, are typically in the form of a gel in the ink of the present invention, while the other polymers mentioned above are typically in the form of solutions.

In preferred embodiments, the polymer is poly(lactic acid). Herein, the term "poly(lactic acid)" refers to a poly (lactic acid) homopolymer or a mixture thereof. The poly (lactic acid) homopolymers include those derived from d-lactic acid, l-lactic acid, or a mixture thereof. Poly(lactic acid) is typically prepared by the catalyzed ring-opening polymerization of the dimeric cyclic ester of lactic acid, which is referred to as "lactide." Poly(lactic acid) may also be made by living organisms such as bacteria or isolated from plant matter that include corn, sweet potatoes, and the like. Poly(lactic acid) made by such living organisms may have higher molecular weights than those made synthetically. In preferred embodiment, the poly(lactic acid) is that sold under number PLA 4032D by Natureworks LLC. This polymer is preferably used in the form of a solution in the ink of the present invention.

In alternative preferred embodiments, the polymer is chitosan. Chitosan is produced commercially by deacetylation of chitin, which is the structural element in the exoskeleton of crustaceans (such as crabs and shrimp) and cell walls of fungi. The degree of deacetylation (% DD) can vary and, in commercial chitosans, ranges from 60 to 100%. On average, the molecular weight of commercially produced chitosan ranges from a few thousand to several hundred thousand Daltons. Chitosan is preferably used in the form of a gel in the ink of the present invention.

The solvent may be any volatile solvent capable of dissolving the polymer or forming a gel of the polymer as well as being capable of dispersing carbon nanotubes. In preferred embodiments, the solvent is dichloromethane (DCM), chloroform ($CHCl_3$), tetrahydrofuran (THF), acetone, methanol (MeOH), ethanol (EtOH) or water.

In embodiments where the polymer (for example poly (lactic acid)) is used in the form of a solution, the solvent is preferably dichloromethane, chloroform, tetrahydrofuran, acetone, methanol, or ethanol, more preferably dichloromethane.

In alternative embodiments where the polymer (for example chitosan) is used in the form of a gel, the solvent is preferably water.

In embodiments, the ink further comprises one or more additives. Non-limitative examples of such additives include:
- glycerol (with a view to conferring flexibility to the 3D printed structure),
- pigments to change the color of the ink,
- short carbon fibers, fiberglass, and/or boron nitride to change the mechanical properties of the ink, and/or
- carbon black spheres, graphene, silver nanowires, copper, and/or nickel nanotubes to change the electrical properties of the ink.

Other examples of additives include acids and bases, preferably acids. Preferably, the acids and bases are used when water is the solvent for the polymer (preferably chitosan) in the ink. In such cases, the acids and bases change the pH and/or the rheological properties (in particular, the viscosity) of the ink. In particular, acids decrease both the pH and the viscosity of chitosan hydrogels. The acids and bases are preferably weak acids and bases. Weak bases and acids are defined as bases and acids that do not ionize fully in an aqueous solution. Typically, weak acids have a $pK_a$ between about −2 and about 12, preferably between about 2 and about 8, and more preferably between about 3 and about 6.5. Typically, weak bases have a $pK_b$ between about −2 and about 13, preferably between about −2 and about 2, and the base has more preferably a $pK_b$ of about 0.2 These acids and bases are preferably organic. These acids and bases are preferably non-toxic. Non-limiting examples of acids include acetic acid, lactic acid, citric acid as well as mixtures thereof. A preferred acid is acetic acid alone or together with one or more other acids such as lactic acid and/or citric acid. Preferably, the total acid concentration ranges from about 40 to about 90 wt % (based on the total weigh of the solvent and the acid(s)). Preferably, the solvent for the ink is water and comprises 70 vol % acetic acid alone or together with 10 vol % lactic acid and 3 wt % citric acid, the vol % being based on the total volume of the water and acids and the wt % being based on the total weight of the water and acids.

In particular embodiments, the ink comprises a gel of chisotan in water (hydrogel) containing one or more non-toxic acids, preferably 70 vol % acetic acid alone or together with 10 vol % lactic acid and 3 wt % citric acid. In such cases, the ink could be used to print biomaterials and materials for biomedical applications as well as any other electrically conductive materials for which the use of toxic solvents is not allowed or is undesirable.

3D Printer Ink Cartridge

In another aspect, the present invention provides a 3D printer ink cartridge, the cartridge comprising a container having an ink outlet, the container comprising the ink as described in the previous section.

In embodiments, the cartridge is adapted to be installed on a 3D printer.

In embodiments, the cartridge is adapted to be fitted to a needle for delivering the ink, so that, for ink dispensing, the ink is extruded through the ink outlet and through the needle.

In embodiments, the cartridge is designed so that when a pressure is applied by a 3D printer, the ink is extruded through the ink outlet.

Method of Manufacture of an Ink for Solvent-Cast 3D Printing

In another aspect, the present invention provides a method of manufacture of the above ink for solvent-cast 3D printing, the method comprising the steps of:
a) providing a solution or a gel of a polymer in a solvent,
b) providing carbon nanotubes in a carbon nanotubes:polymer weight ratio of between about 20:80 and about 40:60,
c) dispersing the carbon nanotubes in the solution or gel of the polymer by ball milling, thereby producing the ink, and
d) avoid drying the ink, thus keeping the solvent in the ink, until the ink is used for solvent-cast 3D printing.

In this method, the ink, the polymer, the solvent, the solution or gel, the carbon nanotubes, their concentrations, their preferred embodiments, etc. are as described above.

As the polymer is soluble in the solvent or can form a gel with the solution, the solution or gel in step a) can be prepared simply by mixing the polymer in the solvent until the polymer is dissolved or the gel is formed. In embodiments, the polymer concentration of this solution or gel is:
- about 2 wt %, about 3 wt %, about 4 wt %, about 5 wt %, about 6 wt %, about 7 wt %, about 8 wt %, about 9 wt %, or about 10 wt % or more and/or
- about 15 wt %, about 14 wt %, about 13 wt %, about 12 wt %, about 11 wt %, or about 10 wt % or less, based on the total weight of the solution or gel. In preferred embodiments where the polymer is PLA, the polymer concentration of this solution or gel is about 10 wt %, based on the total weight of the solution or gel. In preferred embodiments where the polymer is chitosan, the polymer concentration of this solution or gel is about 4 wt %, based on the total weight of the solution or gel.

The dispersion of the carbon nanotubes in step c) is carried by ball milling. Ball milling should be carried out with sufficient energy and for sufficient time so that carbon nanotubes are dispersed in the solution or gel. Generally, a milling time of 10 to 30 minutes, preferably 30 minutes, should be sufficient.

In step d), the solvent is kept in the ink until it is used. The present inventors have found that for carbon nanotubes:polymer weight ratio of about 20:80 or more, the ink must not be dried, particularly when the polymer is PLA (less so when the polymer is chitosan). If it is, it cannot be simply and fully re-dissolved afterwards, which impedes its use (see Examples 1 and 2 for details). Therefore, step d) recites that drying the ink is avoided.

In embodiments, the method further comprises the step of adding solvent, or removing part (for example by partial evaporation) of the solvent. This allows adjusting the polymer and carbon nanotubes total concentration in the ink in the desired range (between about 20 and about 35 wt %, based on the total weight of the ink). Preferred ranges are as noted in the previous section. It should be noted that even when this step is carried out, the condition set out in step d) is respected and the ink is not fully dried, as only part of the solvent is removed from the ink.

In embodiments, the method further comprises, the step of adding one or more additives to the solvent before it is used to form a solution or gel of the polymer, to the solution or gel of the polymer or to the ink. The step at which this additive is added and how it is mixed may vary depending on the additive. In preferred embodiment, the additive is added to the solution or gel of polymer before step c), and mixed in the ink during step c). In alternative embodiments, the additive is mixed into the ink after step c). When the additive is a base or acid, it is preferably added to the solvent before it is used to produce the solution or gel of the polymer (i.e. prior to step a)).

In embodiments, the method further comprises, the step of packaging the ink in a 3D printer ink cartridge.

Method of Manufacturing a Solvent-Cast 3D Printed Material

In another aspect, the present invention provides a method of manufacturing a solvent-cast 3D printed material, the method comprising the steps of:
  a) providing a solvent-cast 3D printing ink as defined above;
  b) using a 3D printer, extruding the ink through a needle into a controlled pattern; and
  c) allowing solvent evaporation, thereby providing the solvent-cast 3D printed material.

Herein, a "controlled pattern" refers to a pattern with a controlled morphology, such as that obtained by 3D printing from a model. Controlled patterns do not include random pattern such as those obtained by simple extrusion, electrospinning or other such methods. However, controlled patterns include patterns involving so-called freeform printing, i.e. patterns including one or more structures printed in the vertical direction with no adjacent supporting layers (e.g. a column). The controlled pattern is typically a layered pattern.

In embodiments of this method, providing step a) include the method of manufacture of a solvent-cast 3D printing ink described in the previous section.

In view of the above information regarding the difficulty in re-dissolving the ink once dried, it will be understood that the solvent should ideally be kept in the ink until the ink is used in step b). In other words, one should avoid letting the ink dry before using it for 3D printing.

It is to be understood that solvent evaporation (in step c) typically begins as soon as the ink is extruded out of the needle in step b).

The speed of the extrusion depends on many interrelated ink- and printer-related factors. These factors include the inner diameter of the needle, the applied pressure, the displacement speed of the needle, the volatility of the solvent, concentration of CNTs, and the viscosity of the ink. For any given ink and desired needle diameter, the remaining printer-related factors are adjusted to allow successful deposition into the desired pattern.

Exemplary 3D printing conditions include:
  an applied pressure between about 2.1 and about 4.2 MPa,
  a displacement speed of the needle ranging from about 0.3 to about 10 mm/sec; and/or
  an inner diameter of the needle ranging from about 100 μm to about 410 μm.

Solvent-Cast 3D Printed Material

In another aspect, the present invention provides a solvent-cast 3D printed material.

This material is shaped into a controlled pattern made of a composite comprising a polymer and carbon nanotubes dispersed in a matrix of the polymer, the carbon nanotubes being present in a carbon nanotubes:polymer weight ratio between about 20:80 and about 40:60.

This material has been manufactured by solvent-cast 3D printing, preferably according to method described in the previous section, from the ink for solvent-cast 3D printing described above. Thus, the nature of the polymer and nanotubes, their preferred concentration, optional additives, etc. are as described above.

This material is electrically conductive; the conductivity increasing with the carbon nanotubes:polymer weight ratio. This makes the material useful for many applications including those described in the next section.

Applications of the Solvent-Cast 3D Printed Material

In embodiments, the above solvent-cast 3D printed material is used as a liquid sensor.

This sensor function is based on electrical conductivity alteration when the 3D printed material enters in contact with a liquid. Indeed, in embodiments, the conductivity varies when the 3D printed material enters in contact with a liquid due to swelling. The liquid enters the polymer matrix, expands this structure and increases the distance between the nanotubes, which decreases conductivity. Such liquid sensor could be used for sensing the concentration of methanol in fuel cells and detecting solvent leakage, thus acting as a security control in pipelines, refineries, gas stations, and automobiles.

There is thus provided a liquid sensor comprising the above 3D printed material. There is also provided the use of the above 3D printed material as a liquid sensor.

In embodiments, the above solvent-cast 3D printed material is used as an electromagnetic interference (EMI) shield. EMI shielding protects sensitive electrical devices from interferences of electromagnetic (EM) radiations emitted by other devices.

Such EMI shielding may be useful, in particular, when light materials are required such as in airplanes, laptops, smart textiles, and cellphones.

There is thus provided an electromagnetic interference (EMI) shield comprising the above 3D printed material. There is also provided the use of the above 3D printed material as an electromagnetic interference (EMI) shield.

Advantages of the Invention and Other Applications

In one or more embodiments, the present invention may present one or more of the following advantages.

The solvent-cast 3D printed material has high electrical conductivity. Thus, only low electrical voltages, such as that provided by 1.5 V of AAA batteries, are required for their functionality. For example, the ink used to make 3D printed scaffolds with a CNT:PLA weight ratio of 30:70, has an electrical conductivity up to about 5100 S/m (when measured as a hot pressed material, see Examples 1 and 2 below).

In embodiments, the 3D printed material is furthermore light and/or flexible and/or shaped into a complex structure.

Highly conductive 3D printing inks open the gate for various applications where conductive structures are made from a polymer based composite. 3D printing enables forming, changing and adjusting the desired structure of the 3D printed material simply by changing the digital model used for printing.

Applications include connecting different parts of a circuit to each other by printing conductive interconnections. Printing these interconnections in 3D will make the circuit more compact, which will lead to improved efficiency.

Electrical components such as resistors, capacitors and transistors can also be printed. Resistors with different resistivity can be made by varying the carbon nanotubes:

polymer ratio or by changing the length of the printed resistors. The conductive connections between the source, drain and gate in a transistor can be printed using the conductive inks.

It is also possible to manipulate the electrical properties of the 3D printed material. For example, capacitors can be fabricated by using a dielectric polymer dissolvable in a volatile solvent as the polymer in the ink.

Various types of sensors such as strain/stress, liquid or gas sensor with 3D configurations can be printed and their structure can be tuned.

Definitions

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% or plus or minus 5% of the numerical value qualified.

Unless otherwise defined, all technical and scientific terms used herein have the same meaning as Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples.

Example 1—Conductive Polymer Based Inks 1.1. Experimental Details

Conductive inks for solvent-cast 3D printing were prepared from highly conductive polymer based composites (hereinafter CNT/PLA-DCM composites) with very high concentrations (up to 40 wt. %) of carbon nanotubes (CNTs).

1.1.1 Composites

Carbon nanotubes (Nanocyl NC7000) were dispersed in PLA (PLA 4032D, Natureworks LLC) by ball mill mixing (SPEX SamplePrep 8000M Mixer/Mill). More specifically, a solution of PLA in DCM with PLA concentration of 10 wt % (based on the total weight of the solution) was placed inside a ball mill vial together with the required amount of CNTs (depending on the desired CNT/PLA ratio) and ball milled for 30 minutes. After mixing, CNT/PLA-DCM composites with CNT concentrations of 2, 5, 10, 20, 30, and 40 wt % (based on the total dry weight of the composite, i.e. the weight of PLA+CNT) were obtained.

1.1.3 Inks and Solvent-Cast 3D Printing

PLA/CNT conductive inks for 3D printing were prepared using the composites obtained in 1.1 above by adjusting the amount of DCM to obtain a proper viscosity for 3D printing. A total concentration of PLA+CNT of 25-30 wt % (based on the total weight of the ink) was used.

For CNT concentrations below 20% (based on the total dry weight of the composite, i.e. the weight of PLA+CNT), the composites and ink could be dried if desired, stored and then dissolved again in the right amount DCM by adding DCM to PLA+CNT in a sealed sample bottle for 24h to obtain the desired viscosity before use. However, for CNT concentrations of 20% or more, if the composite or ink was dried, it could not be fully dissolved again by adding solvent and simple mixing, rather it was necessary to use ball milling to do dissolve the composite. Therefore, these composites were not dried before use. Rather, the amount of DCM was adjusted (usually by partial evaporation) to obtain the desired viscosity. Then, the ink was then used or stored in a hermetical container until use.

For solvent-cast 3D printing, the ink was fed to a syringe which was then placed inside a syringe chamber of dispensing robot (Fisnar I&J2200-4). The extrusion pressure was controlled by a pressure regulator (HP-7X, EFD) set in range of 2.1-4.2 MPa in order to match the displacement rate of the robot ranging from 0.3 to 1 mm/sec. The selected values of the applied pressure and displacement of the nozzle depended on the concentration of CNTs and the viscosity of the prepared ink. The syringes and micro-needles ranging from 100 µm to 330 µm were supplied by Nordson EFD Company.

1.1.4 Electrical Conductivity Measurements

These tests were carried in the same manner as in Example 2 below.

1.1.5 Liquid Sensor

These tests were carried in the same manner as in Example 2 below.

1.1.6 Electromagnetic Interference (EMI) Shield

EMI shielding measurements were performed over the X-band (8.2-12.4 GHz) frequency range using an E5071C network analyzer (ENA series 300 KHz-20 GHz). EMI shielding effectiveness (EMI SE) is defined as the logarithm of the ratio of the incident power to the transmitted power and is reported in dB unit. The EMI SE and error bar values are the average and standard deviation values of the overall EMI SE data over the X-band frequency range, respectively. The samples were placed between two X-band waveguide parts, connected to separate ports of the network analyzer. The network analyzer sent an electromagnetic wave onto the sandwiched sample and the powers of the incident, reflected and transmitted waves were measured by three wave detectors to calculate EMI SE.

1.2. Results 1.2.1 Composites

PLA/CNT composites with various CNT concentrations in the range of 0 to 40 wt. % were fabricated and their electrical conductivities were measured using four-point probes (see FIG. 1). The conductivity of CNT/PLA composites reached a maximum of about $1.7\times10^4$ S/m for a CNT concentration of 40 wt. %.

1.2.2 Solvent-Cast 3D Printing (SC-3DP)

The maximum CNT concentration and conductivity of the fabricated printable ink was 30 wt. % and ~5100 S/m, respectively. A comparison of the electrical conductivity of the fabricated inks to other reported polymer based conductive composites suitable for 3D printing demonstrates its high conductivity (see S. J. Leigh, R. J. Bradley, C. P. Purssell, D. R. Billson, D. A. Hutchins, Plos one 2012, 7(11); G. Postiglione, G. Natale, G. Griffini, M. Levi, S. Turri, Composites Part A: Applied Science and Manufacturing 2015, 76, 110; and S. Z. Guo, F. Gosselin, N. Guerin, A. M. Lanouette, M. C. Heuzey, D. Therriault, Small 2013, 9, 4118).

The SC3DP method enabled us to use inks with high concentrations of CNT because the viscosity of the ink could be adjusted by varying the concentration of ink's solvent.

Figure 2:
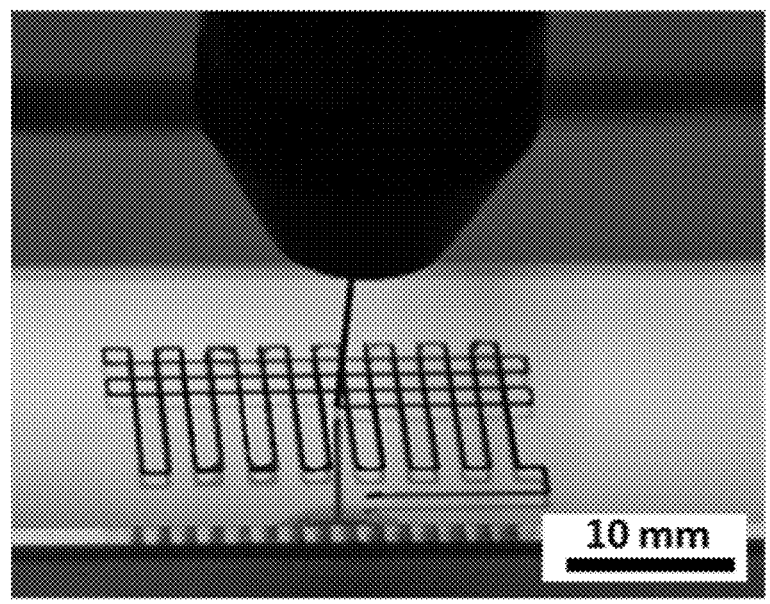
FIG. 2 shows the 3D printing of scaffolds by solvent cast 3D printing using a nozzle with a 200 μm inner diameter.
Figure 3:
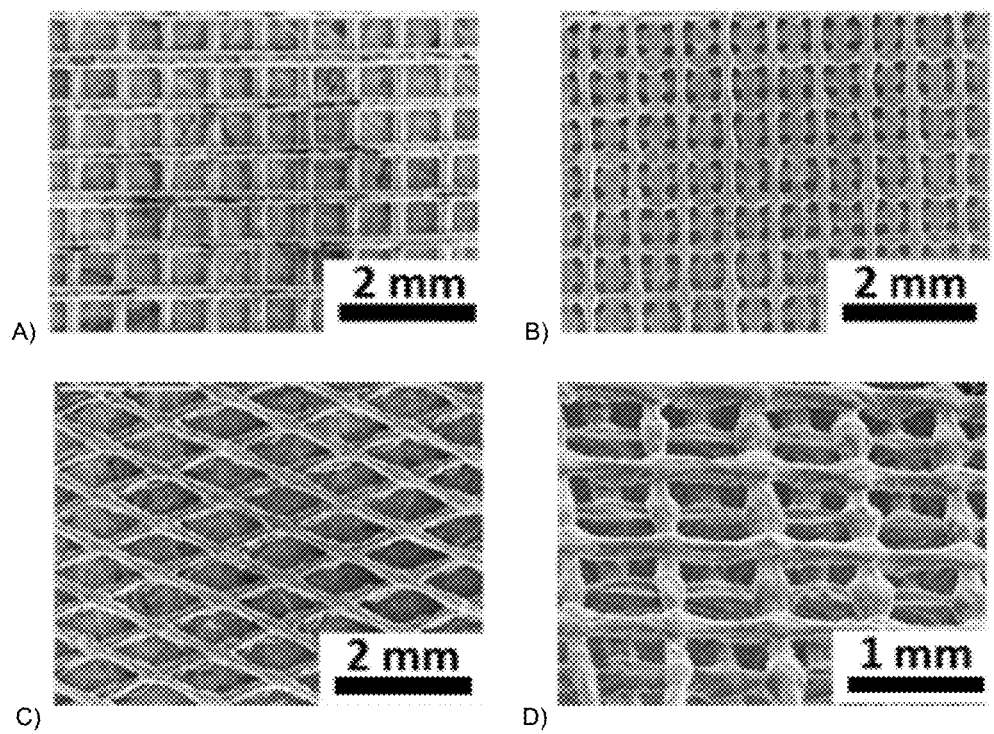
FIG. 3 shows SEM images of scaffolds fabricated in different patterns: A) an open window pattern (top view), B) a closed window pattern (top view), C) a Zigzag pattern (top view), and D) a square pattern (3/4 view)

Scaffold structures with different structural parameters (e.g., inter-filament spacing, number of layers and filament diameters) were fabricated using SC-3DP method. FIG. 2 shows the actual printing, while FIG. 3 shows SEM images of printed scaffolds with different structural patterns.

Figure 4:
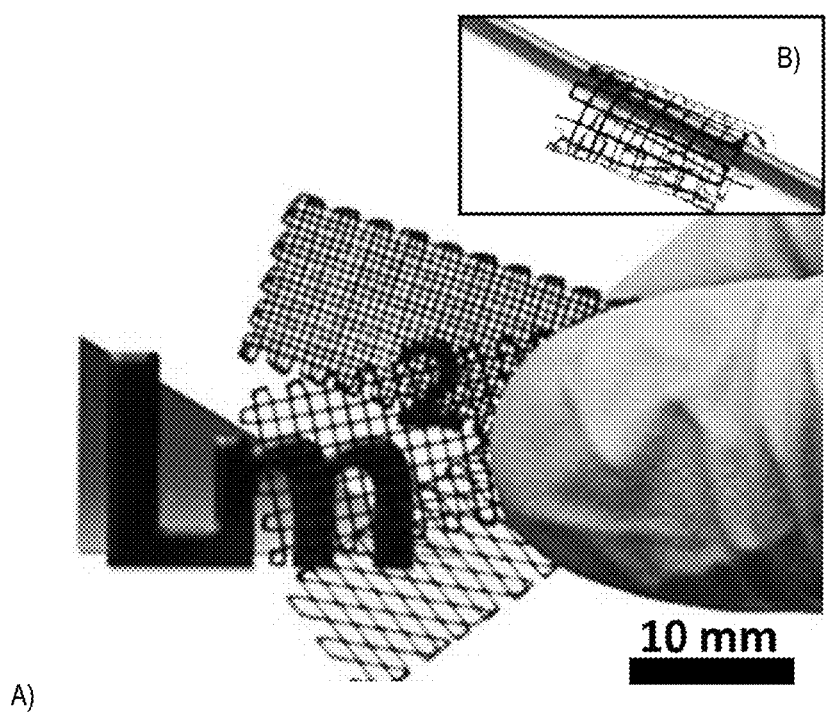
FIG. 4 A) shows three 4-layered printed scaffolds with different printed patterns and B) (inset photo) shows a scaffold printed in 2 layers wrapped around a cylinder.

FIG. 4 shows three 4-layered printed scaffolds with different printed patterns but similar IFS, showing the transparency of the scaffolds. The Zigzag and open window patterns showed much better transparency compared to the closed window pattern. The inset photo (B) is a scaffold printed in 2 layers wrapped around a metal bar showing its flexibility.

The application of conductive scaffold (with open window pattern) as liquid sensors and EMI shielding was investigated for CNT concentrations ranging between 0 to 30 wt. % with varying inter-filament spacing (IFS) and numbers of layers.

Figure 5:
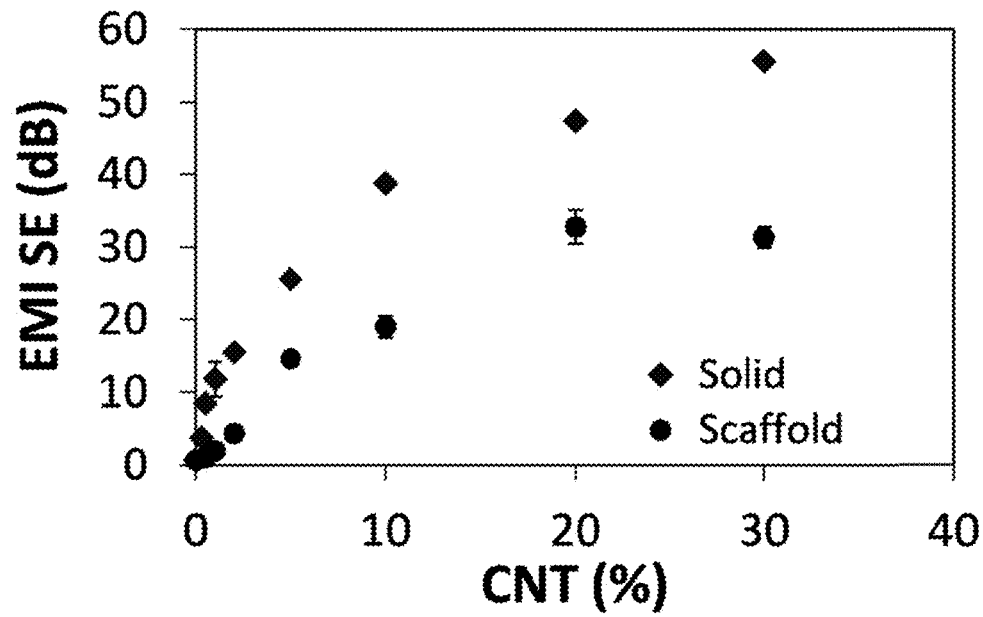
FIG. 5 shows the EMI shielding effectiveness (EMI SE) of the 3D printed scaffold as a function of CNT concentration.
Figure 6:
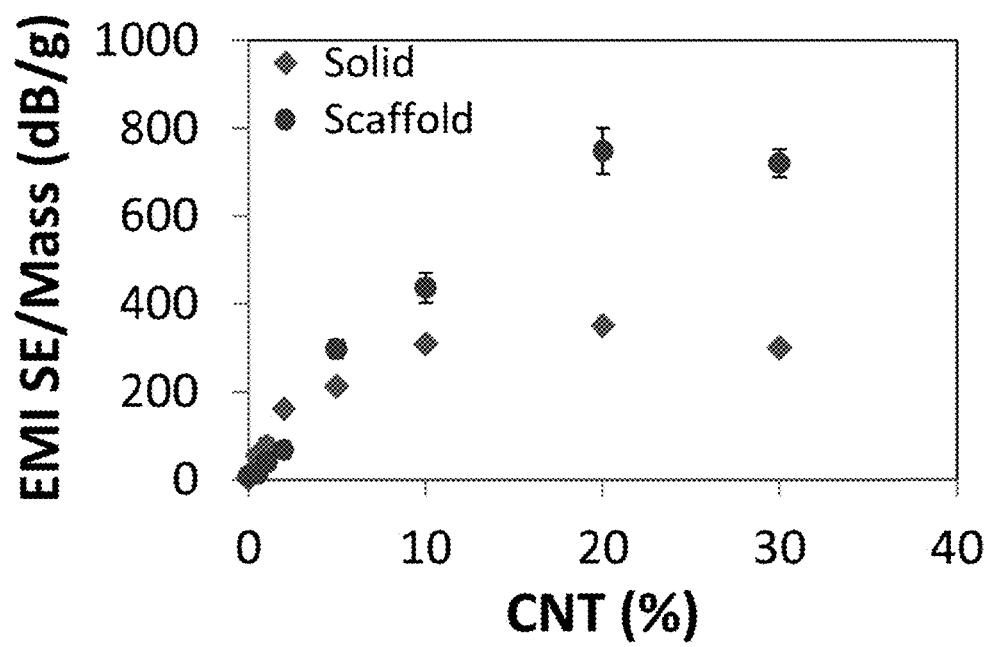
FIG. 6 shows the EMI shielding effectiveness (EMI SE) normalized by mass of the 3D printed scaffold as a function of CNT concentration.

FIG. 5 shows that the EMI shielding effectiveness (EMI SE) increases with increasing CNTs concentration in the inks. The EMI SE reached as high as about 55 dB and 33 dB for the CNTs/PLA in form of solid and scaffold samples, respectively.

FIG. 5 shows the EMI shielding effectiveness (EMI SE) normalized by mass. Higher efficiencies are observed in the case of conductive scaffolds compared to a solid form. The difference in efficiency could reach to about two times for the CNT/PLA with CNTs concentration of 30 wt. %.

Figure 7:
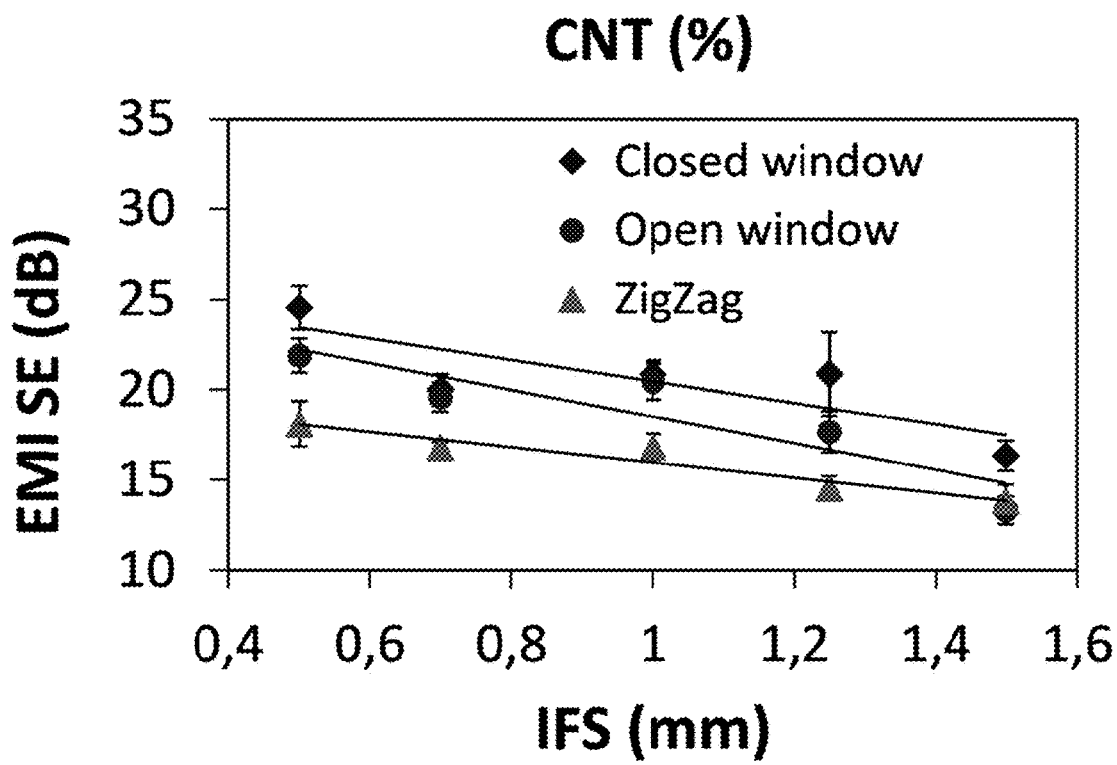
FIG. 7 shows the EMI shielding effectiveness (EMI SE) of the 3D printed scaffold as a function of inter-filament spacing (IFS)

FIG. 7 shows the EMI SE as a function of IFS. There is a slight decrease in EMI SE when increasing IFS. This decrease can be related to the fact that by increasing the distance between the filaments lower mass of conductive material is used in the equal surface areas leading to lower shielding efficiency.

Figure 8:
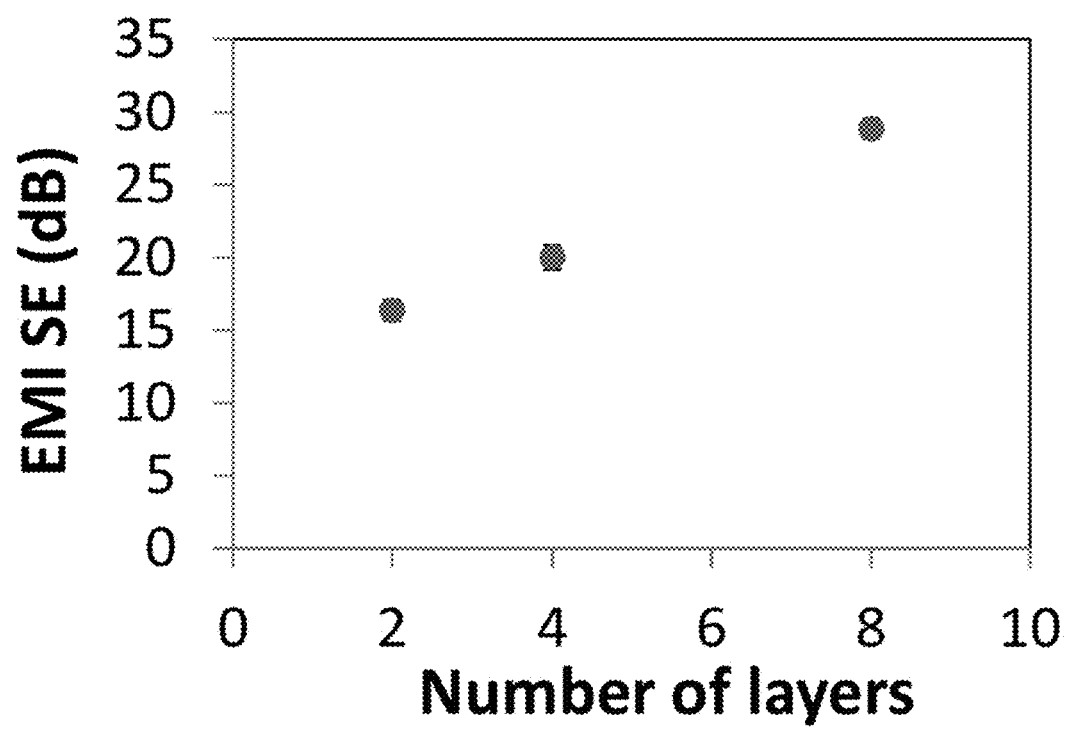
FIG. 8 shows the EMI shielding effectiveness (EMI SE) of the 3D printed scaffold as a function of the number of layer.

FIG. 8 shows the EMI SE as a function of the number of layers. Increasing the number of printed layers led to an increase in EMI SE which can be useful for the application of these conductive scaffolds as semi-transparent EMI shielding structures. The shielding efficiency can be increased by adding the number of printed layers while there is a slight decrease in transparency (<%5 per layer).

Figure 9:
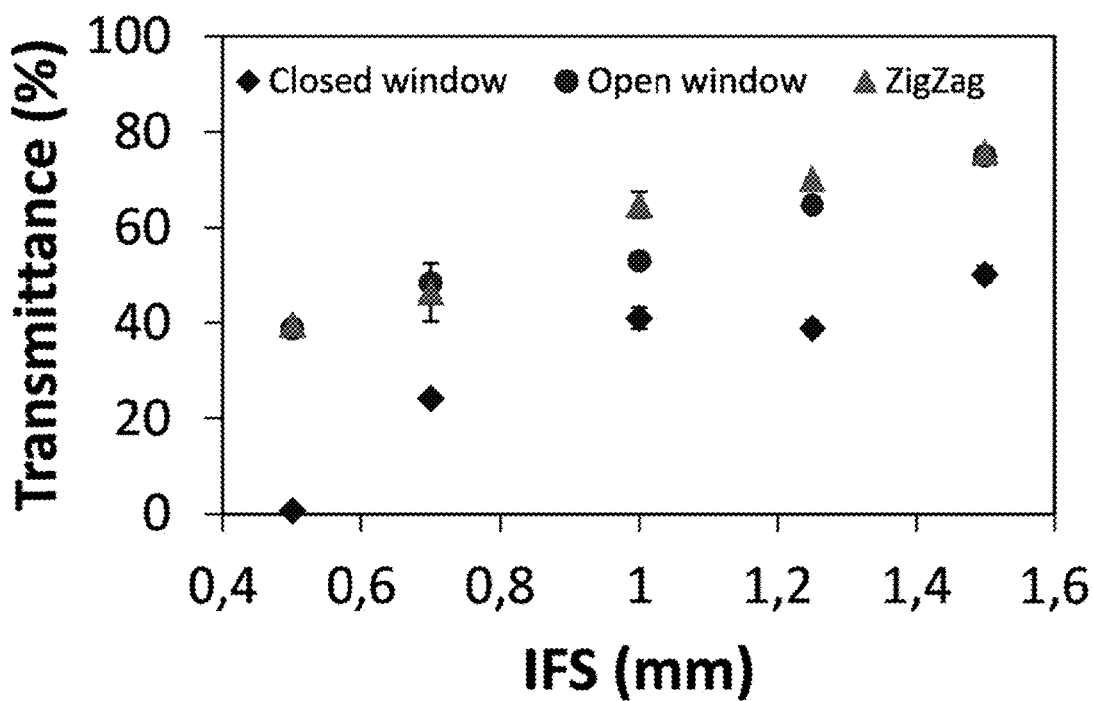
FIG. 9 shows the transmittance of the scaffolds as a function of IFS.

FIG. 9 shows the transmittance of the scaffolds. It increased with increasing IFS since the distance between the filaments increased and lower total mass was used for the equal surface exposed to light. Changing the pattern from closed window to open window or Zigzag increased the light transmittance for about 25%.

Figure 10:
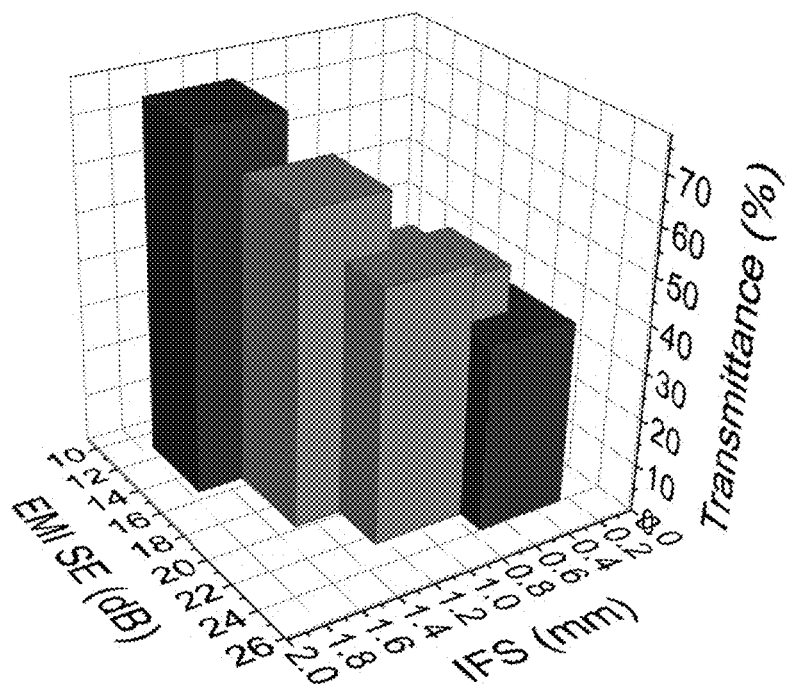
FIG. 10 is a 3D graph showing EMI SE and transparency of the scaffolds as a function of their IFS.

FIG. 10 is a 3D graph showing EMI SE and transparency of the scaffolds as a function of their IFS. Depending on the desired transparency and EMI SE, the IFS and the printed pattern of the scaffold can be adjusted.

Figure 11:
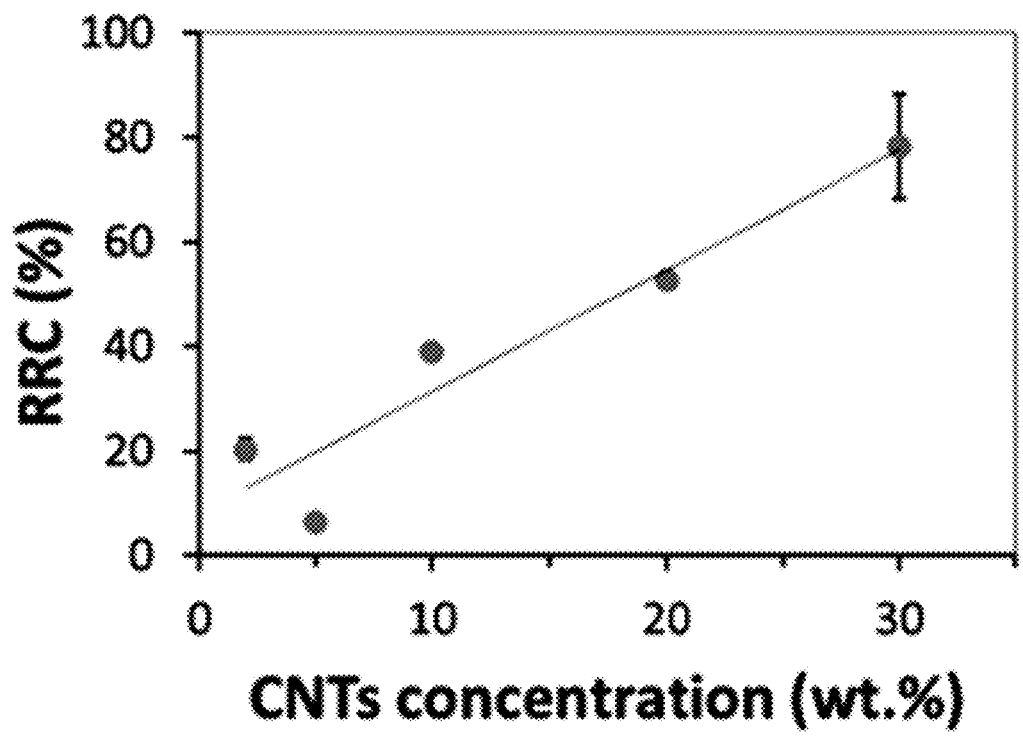
FIG. 11 shows the relative resistance change (RRC) of the 3D printed scaffold when immersed for 120 s in acetone, as a function of time.

FIG. 11 shows the relative resistance change (RRC), which shows the liquid sensitivity of CNT/PLA scaffolds, as a function of CNTs concentration.

Example 2-3D Printing of Highly Conductive Inks

Here we report the fabrication of highly conductive CNTs/PLA 3D printable conductive inks for fabrication of conductive scaffold structures applicable as liquid sensors. 3D printing enables us to control the structural parameters of liquid sensors and study their influence on the sensitivity of the obtained liquid sensor which can be useful for structures made from repeated patterns of filaments, such as for liquid sensors in form of textiles. This work shows how 3D printing can be used to explore experimentally the topology optimization of sensors where their sensitivity is related to their structural parameters.

2.1 Experimental Section

2.1.1 Fabrication of Nanocomposites

Carbon nanotubes (Nanocyl NC7000) were dispersed in the PLA (PLA 4032D, Natureworks LLC) by ball mill mixing (SPEX SamplePrep 8000M Mixer/Mill). More specifically, a PLA solution in DCM with a PLA concentration of 10 wt. % (based on the total weight of the solution) was placed inside a ball mill vial together with the required amount of CNTs (depending on the desired CNT/PLA ratio) and ball milled for 30 minutes. After mixing, composites with CNT concentrations of 2, 5, 10, 20, 30, and 40 wt % (based on the total dry weight of the composite, i.e. the weight of PLA+CNT) were obtained.

2.1.2 Fabrication of 3D Printing Inks

After mixing, the composites with CNT concentrations below 20 wt % (based on the total dry weight of the composite, i.e. the weight of PLA+CNT) were taken out of ball mill vial and dried at room temperature for 24 hours. The obtained CNT/PLA nanocomposites were dissolved in DCM to obtain an ink with a viscosity appropriate for solvent-cast 3D printing (SC-3DP). Thus, inks with a total CNT+PLA concentration of about 25-30 wt % (based on the total weight of the ink) were prepared.

However, for CNT concentrations of 20% or more (based on the total dry weight of the composite, i.e. the weight of PLA+CNT), as noted above, if the composite was dried, it could not be fully dissolved again by adding solvent and simple mixing. Therefore, these composites were not dried before use. Rather, their total CNT+PLA concentration was adjusted to 25-30 wt % (based on the total weight of the ink) by partially evaporating the DCM at room temperature directly after ball mill mixing. Then, the inks were used for 3D printing.

2.1.3 Solvent-Cast 3D Printing of Scaffolds

The ink was fed to a syringe which was then placed inside the syringe chamber of a dispensing robot (Fisnar I&J2200-4). The extrusion pressure was controlled by a pressure regulator (HP-7X, EFD) set in range of 2.1-4.2 MPa in order to match the displacement rate of the robot ranging from 0.3 to 1 mm/sec. The selected values of the applied pressure and displacement rate of the nozzle depended on the concentration of CNTs and the viscosity of the prepared ink. The syringes and micro-needles ranging from 100 μm to 330 μm were supplied by Nordson EFD company.

2.1.4 Conductivity Measurements

The electrical conductivity tests were performed on hot pressed CNT/PLA composites. The CNT/PLA nanocomposites with different CNT concentrations fabricated by ball mill mixing method were compression molded under the pressure of 38 MPa for 5 min using a Carver compression molder (Carver Inc., Wabash, Ind.). A metallic mold with dimensions of 22.9×10.2×0.4 mm$^3$ was used to form a rectangular shaped. The surface of the samples was wiped with ethanol to remove impurities prior to the conductivity measurements. For nanocomposites with electrical conductivities more than $10^{-2}$ S·m$^{-1}$, the conductivity measurements were carried out according to ASTM 257-75 using a Loresta GP resistivity meter (MCPT610 model, Mitsubishi Chemical Co., Japan). A four-point probe was used for all conductivity measurements to avert the effect of contact resistance. A Keithley 6517A electrometer connected to a Keithley 8009 test fixture (Keithley Instruments, USA) was used for the measurements of the nanocomposites with conductivities less than $10^{-2}$ S·m$^{-1}$.

2.1.5 Liquid Sensitivity Tests

The liquid sensitivity of liquid sensors with a scaffold configuration was tested by measuring their electrical resistivity during immersion/drying cycles. Acetone was used as the testing solvent. Scaffolds were cut in U shape using a metallic blade. The bottom part of U-shaped was placed in the solvent and the electrodes of the resistivity meter were attached to the upper extremities. The liquid sensors were immersed inside acetone and their electrical resistivity were tracked using a resistance meter (Keithley 6517B) connected to a PC and a Labview software. Seven immersion/drying cycles were done on each sample and the average value of the last four peaks was used to calculate the RRC and their error bars. The RRC is the percentage of the difference between the actual resistance and the initial resistance to the initial resistance of the liquid sensors. The immersion and drying times were set at 120 s and 600 s, respectively.

2.1.6 Liquid Trapping Tests

Figure 12:
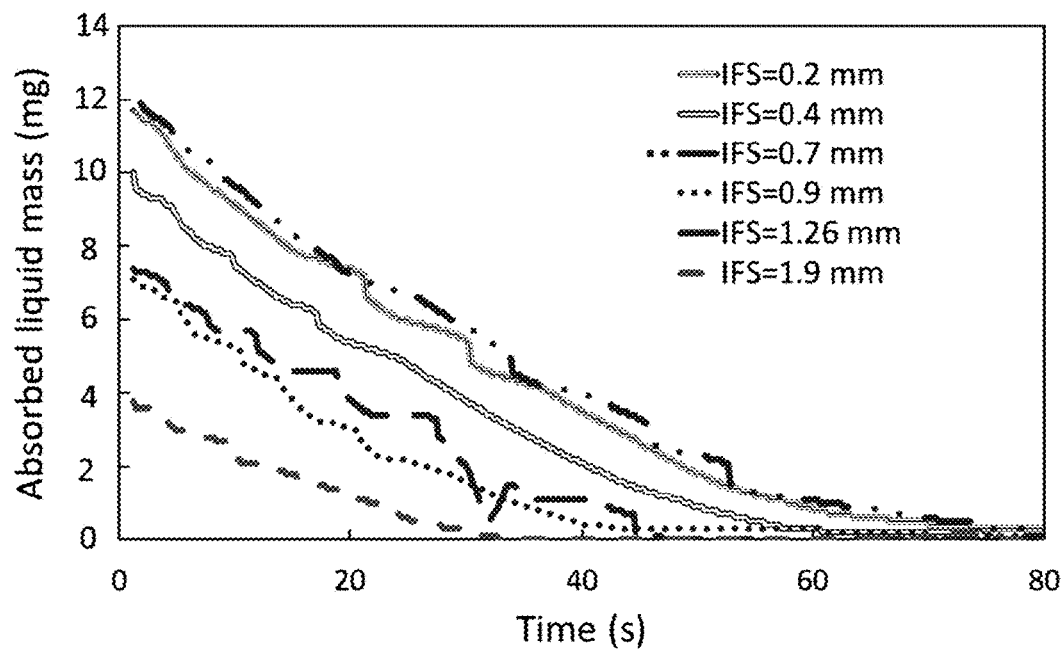
FIG. 12 shows the mass of absorbed liquid as a function of drying time.

To measure the amount of liquid trapped in the structure of the scaffolds, the scaffolds in U shape were hanged to a hook under a digital scale (A&D GH-200). The mass of absorbed liquid was measured during the drying time after they were immersed in acetone. See FIG. 12 showing how the mass of the liquid decreased over time. This measurement repeated for five cycles with the immersion/drying time of $^{20}/_{180}$ seconds. The values of the liquid trapping were calculated from the integral of the curves of mass of absorbed liquid as a function of drying time.

2.2 Results 2.2.1 Fabrication of Nanocomposites and Inks and 3D Printing of Scaffolds Ball mill mixing method enabled us to fabricate CNT/PLA composites with very high CNTs concentration (i.e., up to 40 wt. %) with high electrical conductivities up to abZout 1.7E+4 S·m$^{-1}$S/m).

Figure 13:
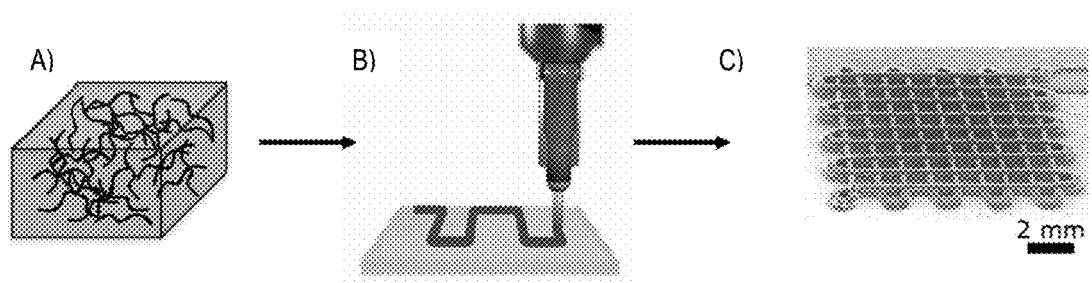
FIG. 13 is A) a schematic of CNT/PLA inks fabricated via ball mill mixing method; B) a schematics of 3D printing method used for fabrication of CNT/PLA scaffold structures; and C) a SEM image of a scaffold printed in two layers using the 3D printing method.
Figure 14:
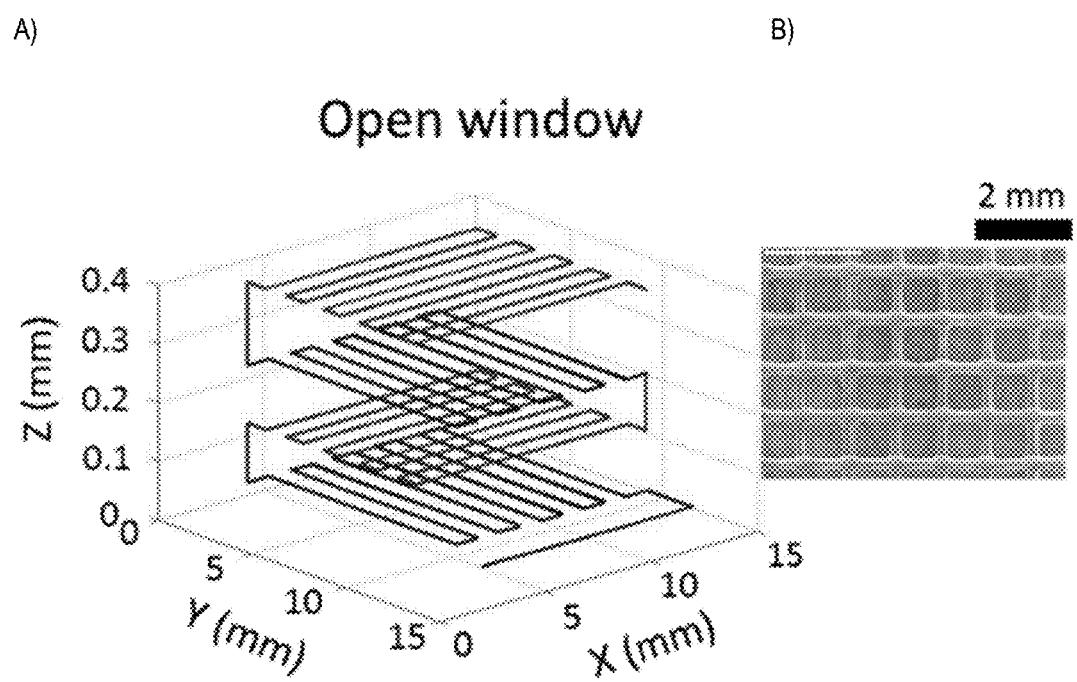
FIG. 14 shows (A) the printing patterns used to print an open window configuration scaffold and (B) the printed scaffold.
Figure 15:
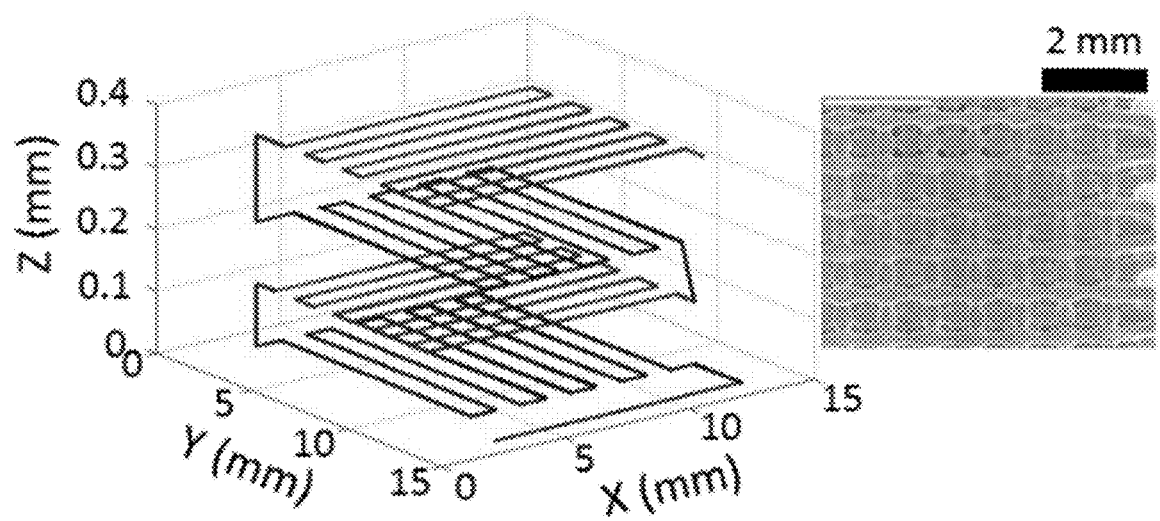
FIG. 15 shows (A) the printing patterns used to print a closed window configuration scaffold and (B) the printed scaffold.
Figure 16:
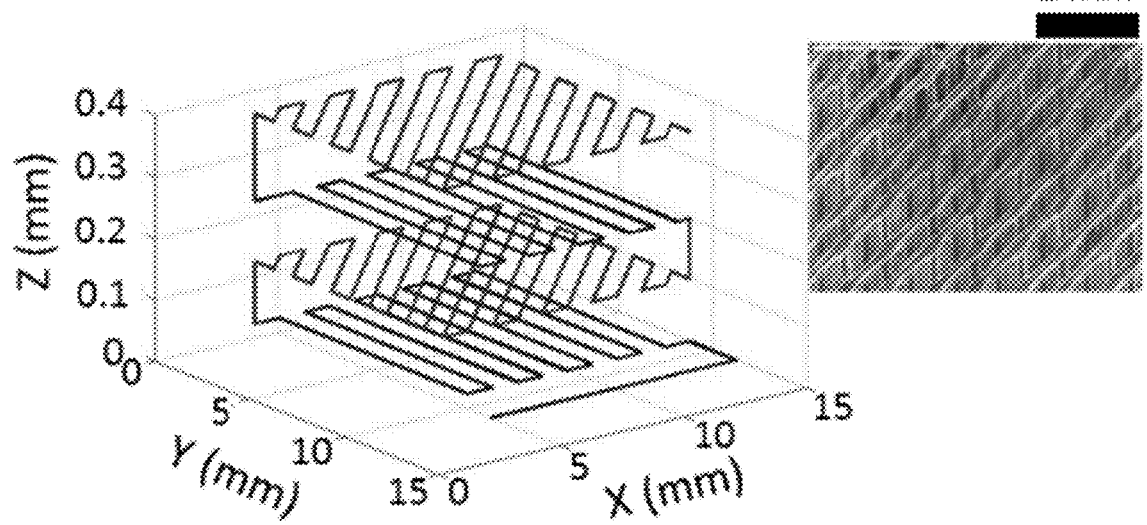
FIG. 16 shows (A) the printing patterns used to print a Zigzag I configuration scaffold and (B) the printed scaffold.
Figure 17:
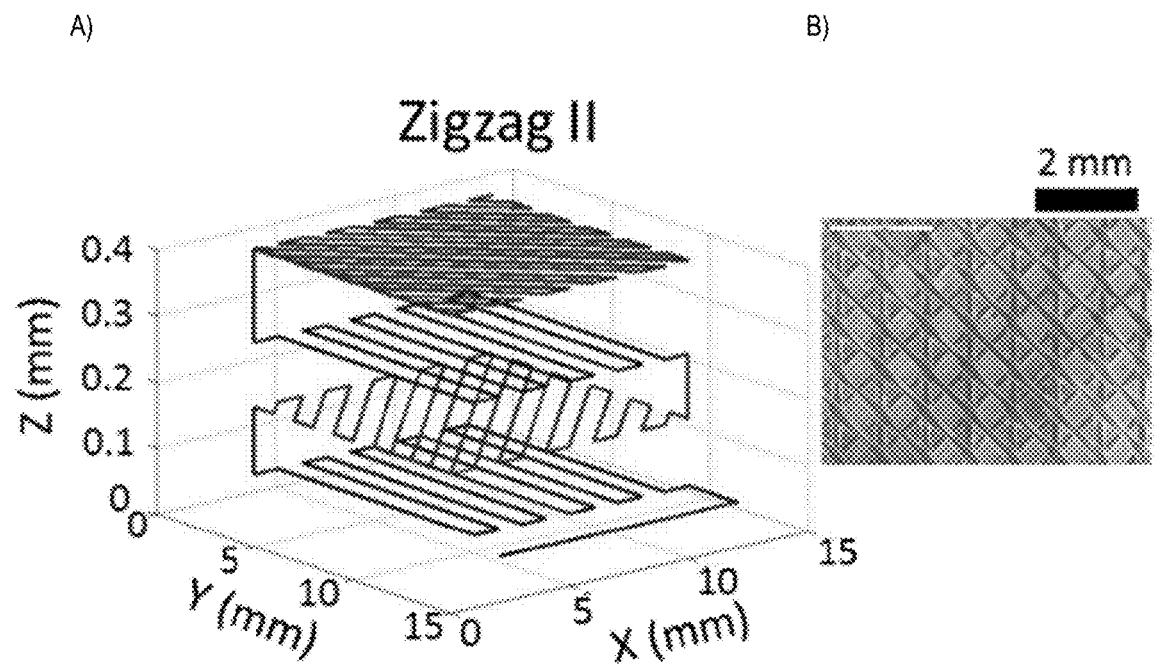
FIG. 17 shows (A) the printing patterns used to print a Zigzag II configuration scaffold and (B) the printed scaffold.

Structures in form of scaffolds with different structural parameters (i.e., filament diameter, inter-filament spacing (IFS), thickness of scaffolds and configuration patterns) were fabricated using solvent-cast 3D printing method. The filament diameters were varied from 128 µm to 432 µm by changing the extrusion nozzle used for 3D printing within the range of 100 to 330 µm. IFS, number of printed layers and the printed patterns were controlled by modifying a computer aided design (CAD) software. FIG. 13 shows schematics and SEM images showing the fabrication and, the configurations of the conductive scaffold structures.

Figure 18:
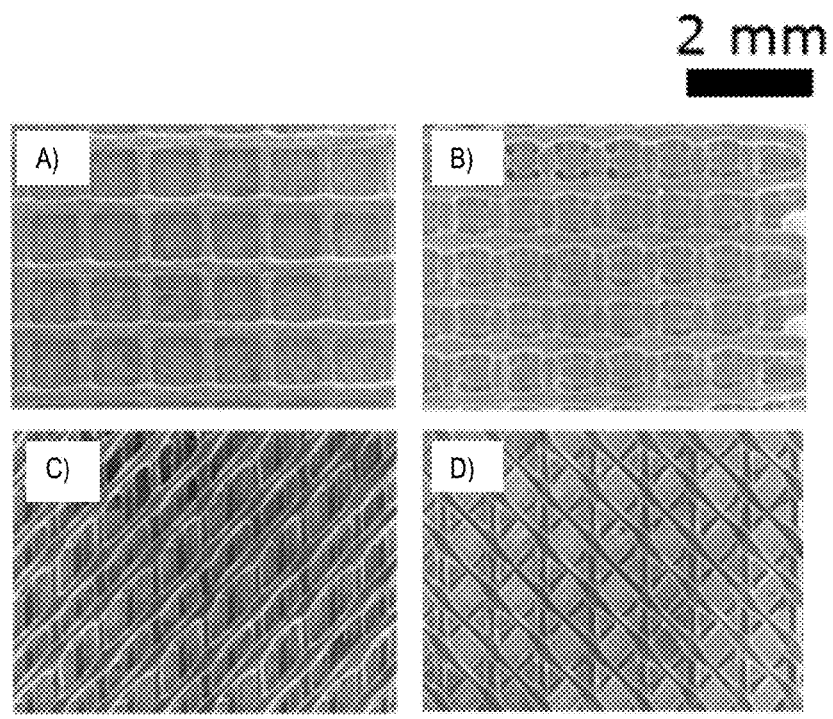
FIG. 18 shows top view of SEM images of scaffolds printed in four layers with different patterns: A) Open window, B) Closed window, C) Zigzag I, and D) Zigzag II.

FIGS. 14-17 shows the printing patterns used for fabrication of the (a) open window, (b) closed window, (c) Zigzag I and (d) Zigzag II configurations. The third and fourth layers in closed window configuration is placed in between first and second layers in a way that they close the windows formed from printing of the first two layers. The insets are the SEM images of each structure. FIG. 18 shows SEM images of different printed patterns denoted as A: open window, B: closed window, C: Zigzag I and D: Zigzag II. The thickness of the scaffolds varied from 0.17 to 1.11 mm by changing the number of printed layers from 2 to 10.

2.2.2 Liquid Sensitivity Tests

Figure 19:
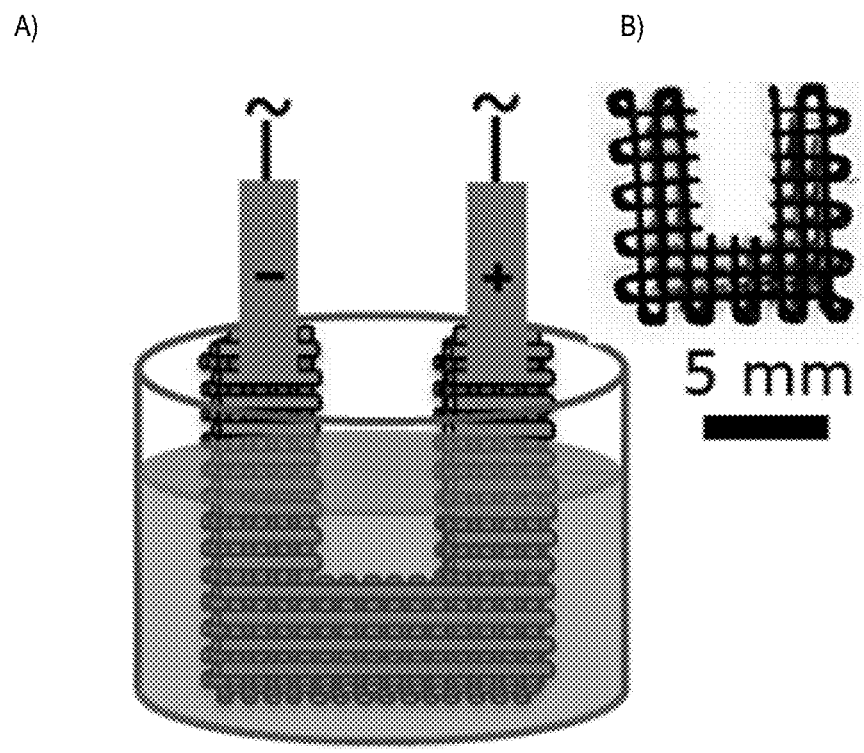
FIG. 19 shows A) the liquid sensitivity testing of U shaped cut scaffold and B) a top view optical image of a U shaped cut scaffold.
Figure 20:
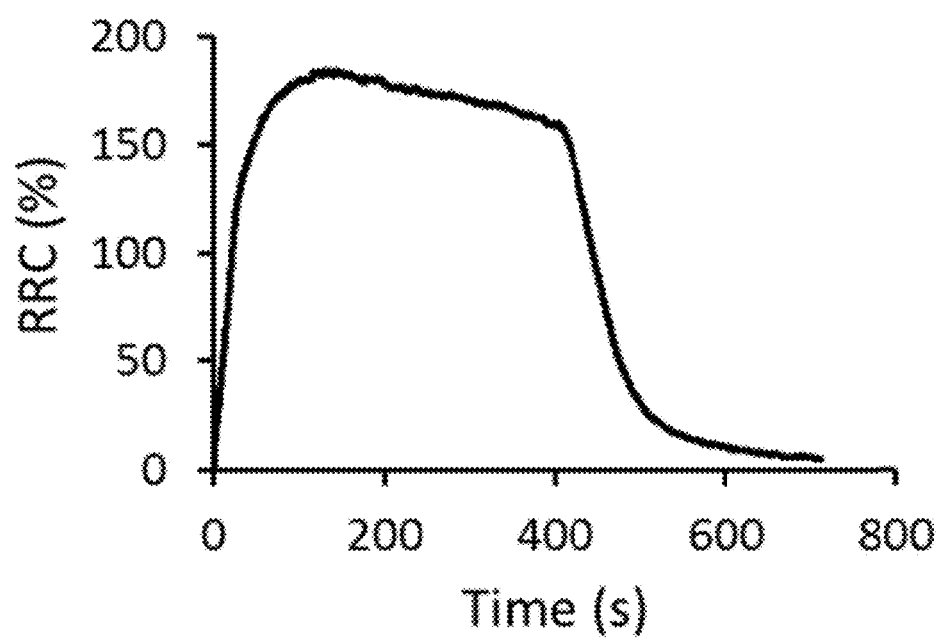
FIG. 20 shows a typical liquid sensitivity test graph.

FIG. 19 shows a schematic and an optical photo of the U shaped cut of the scaffolds used for the liquid sensitivity measurements. They were cut in U shape to have a specific part of the sample immersed in the liquid while the electrodes were connected to the top extremities without contacting with the liquid. A typical graph of relative resistance change (RRC) resulted from an immersion/drying cycle of a scaffold printed with a 200 µm inner diameter nozzle in four layers with IFS of 0.7 mm is shown in FIG. 20. The immersion/drying time was at 120/600 s. FIG. 20 shows the increase and decrease of the RRC of a liquid sensor while immersion/drying cycles. This test was on a scaffold with IFS of ~0.7, thickness of ~0.4 mm and filament diameter of ~231 µm printed in open window pattern.

RRC of the liquid sensor increased while it was immersed in the liquid due to the polymer swelling originated from the diffusion of liquid inside the polymer matrix. RRC decreased gradually when the scaffold was taken out of the liquid. At this time although the scaffold is out of liquid, due to the capillary forces of grid-like structure, it can keep a portion of the liquid inside its structure which slow down the RRC decreasing rate. After about 400 s when the liquid is evaporated and left the structure, the RRC decreased with a faster rate to the initial resistivity. Seven immersion/drying cycles were tested for each sample and the average RRC of the last four cycles, where the liquid sensitivity becomes more stable, were used to compare the sensitivity of liquid sensors with different configurations.

The influence of four different structural parameters (i.e., IFS, filament diameter, scaffold thickness, and structural patterns) on the sensitivity of the printed scaffold liquid sensors was investigated and the results are shown in FIGS. 21 to 24, respectively. Higher RRC values indicates greater sensitivity of the liquid sensors since they show higher electrical resistance variation when immersed in the testing liquid. The schematics on top of the graphs and the fitted curves are illustrated to facilitate the following of the trend of variables and RRC values, respectively.

Figure 21:
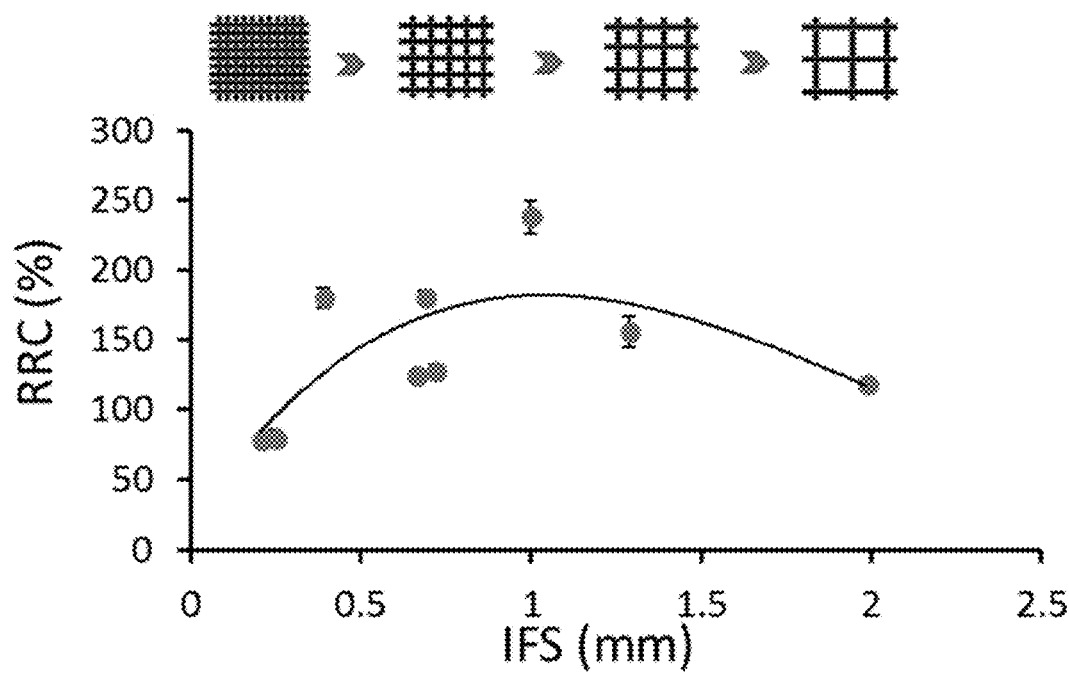
FIG. 21 shows the effect of IFS on the liquid sensitivity of the conductive scaffolds.

FIG. 21 demonstrates the effect of IFS on the sensitivity of the liquid sensors printed in four layers with a nozzle diameter of 200 µm. The average RRC varied from ~78% to ~238% by changing the IFS in the range of 0.2 to 1.9 mm. The lowest liquid sensitivity (i.e., 78%) was related to the scaffold with the lowest IFS which can be considered as the most compact structure. The number of filaments along the length and width of the scaffolds increases by decreasing the IFS leading to more intersections of the top and bottom neighbouring filament layers. The surfaces covered in these intersections are hardly accessible to the liquid and increasing the inaccessible surface area decreases the effect of liquid on the RRC of the liquid sensors. The optimum liquid sensitivity was observed for the scaffolds with IFS in the range of 0.5 to 1.5 where the RRC varied between 124 to 238%. The slight decrease in the sensitivity of the liquid sensors (at 118%) for the liquid sensor with IFS of 1.9 mm can be related to the fact that at higher IFS the scaffolds are less dense and less material contacts the liquid which lowers the total conductivity and the detection of its variation.

Figure 22:
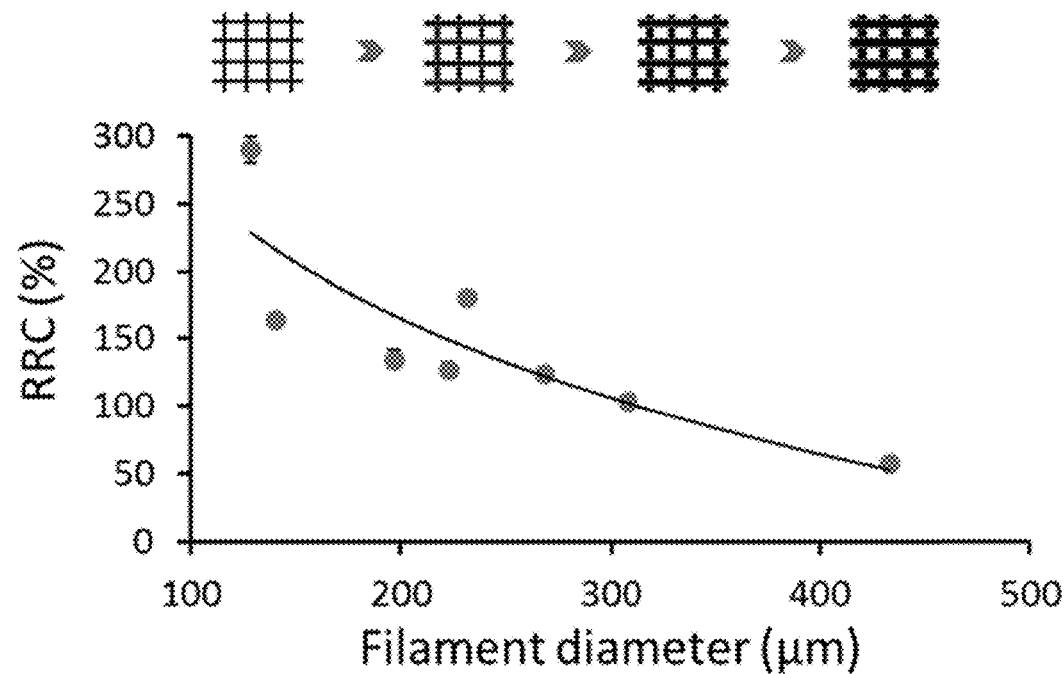
FIG. 22 shows the effect of filament diameter on the liquid sensitivity of the conductive scaffolds.

FIG. 22 shows the influence of the filament diameter on the sensitivity of the liquid sensor printed in four layers and IFS of ~0.7 mm. The highest RRC (i.e., 290%) was obtained at the lowest filament diameter (i.e., 128 µm). This value decreased gradually to 58% by increasing the filament diameter up to 433 µm. The decrease of the liquid sensitivity by increasing the filament diameters might be due to the difference in the liquid diffusion time for the swelling of the filaments. Kobashi et al. (K. Kobashi, T. Villmow, T. Andres, P. Pötschke, Sensors and Actuators B: Chemical 2008, 134, 787) have tested liquid sensors in form of a U shaped bulk solid CNT/PLA with different thicknesses in the range of 0.1 to 0.5 mm and reported a sharper response and faster recovery of the composite electrical resistance during immersion/drying cycles for thinner liquid sensors. In the case of scaffold, since the diffusion pathway is longer for larger filament diameters, the liquid requires more time to fill and expand the PLA matrix which leads to lower sensitivity of the liquid sensor.

Figure 23:
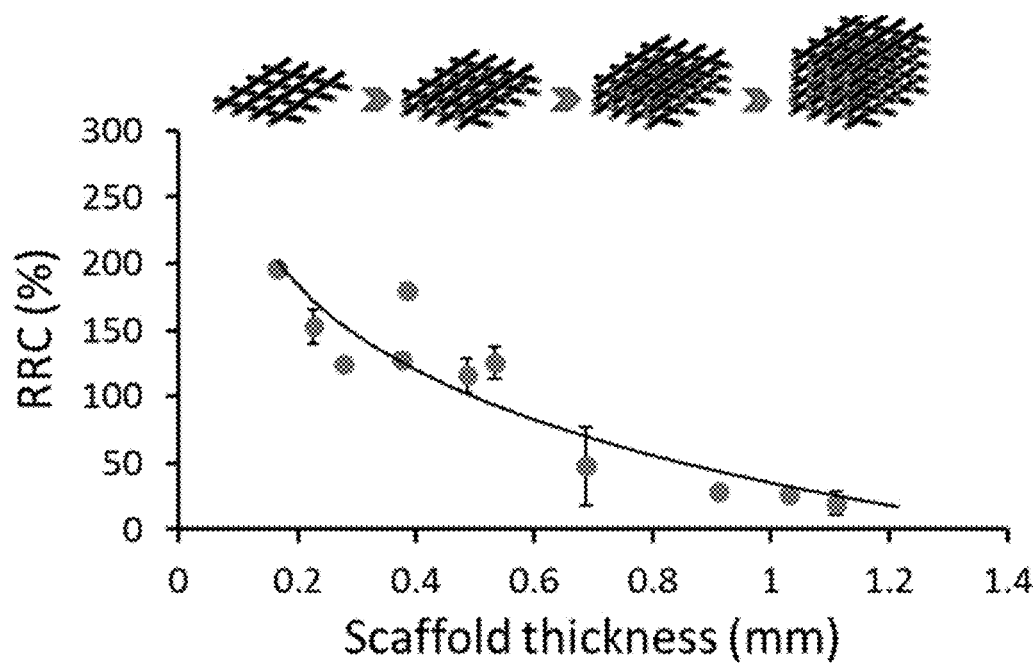
FIG. 23 shows the effect of scaffold thickness on the liquid sensitivity of the conductive scaffolds.

FIG. 23 demonstrates the variation of the RRC as a function of scaffold thicknesses for the scaffolds printed by a nozzle diameter of 200 µm and IFS of ~0.7 mm. Increasing in the scaffold thickness from 0.17 to 1.11 mm led to a decrease in RRC from 196 to as low as 19%. Since the distance between the printed layers are small (e.g., <100 µm), a slight deformation before the total evaporation of DCM, the ink's volatile solvent, during the printing process can cause partial overlapping of these filaments. Increasing the number of printed layers increases the area of these covered surfaces and since the testing liquid has less access to the covered areas, lower sensitivity can be obtained for scaffold liquid sensors with higher number of printed layers.

Figure 24:
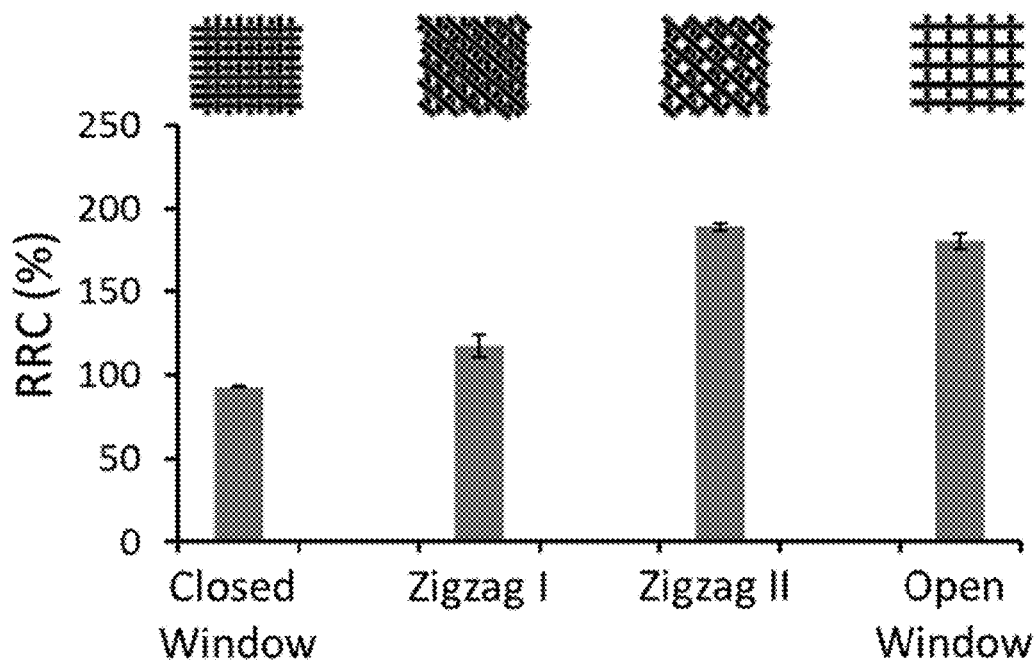
FIG. 24 shows the effect of structure patterns on the liquid sensitivity of the conductive scaffolds.

The liquid sensitivities of the liquid sensors printed in different patterns are demonstrated in FIG. 24. The relative resistance change of the liquid sensors in different scaffold patterns varied between 93 to 188%. Considering the fact that the variation of the relative resistance change for the open window patterns fabricated with similar printing parameters (i.e., IFS: ~0.7, number of layers: 4 and nozzle inner diameter: 200 µm) varied between 123 to 180% (FIG. 21), the effect of pattern variation on the liquid sensitivity was relatively low.

Based on these results the overall optimum structural parameters of a CNT/PLA grid like liquid sensor can be considered for scaffold structure with filament diameter <250 µm, thickness <0.6 mm and IFS between 0.5 to 1.5 mm. The effects of filament diameter and scaffold thickness in the tested ranges are more remarkable compared to the influence of IFS and scaffold pattern on the sensitivity of the liquid sensors.

Figure 25:
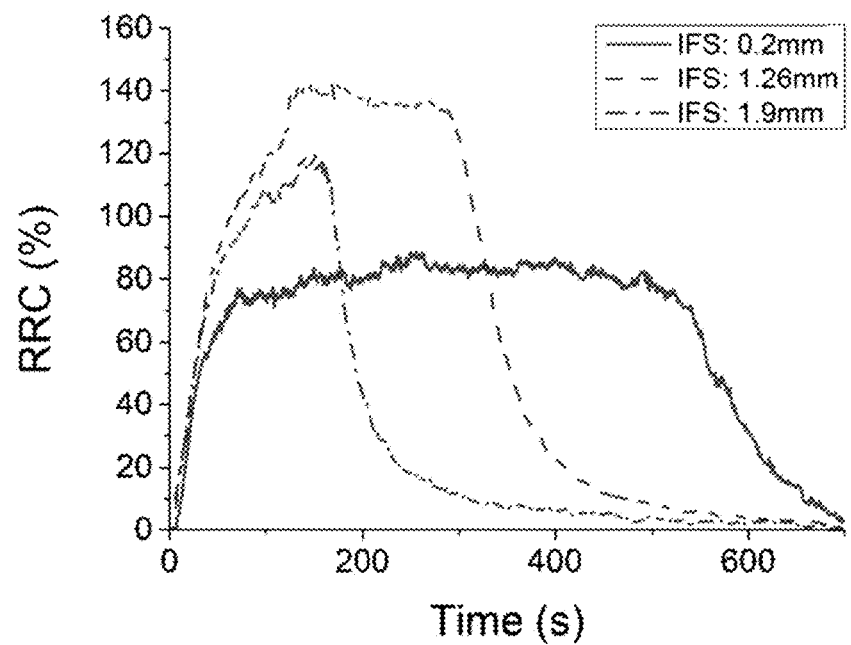
FIG. 25 shows RRC as a function of time during an immersion/drying cycle.

FIG. 25 shows the graph of RRC resulting from an immersion/drying cycle for the scaffolds with three representative IFSs (i.e., 0.2, 1.28 and 1.9 mm). A decrease of the RRC peaks width with increasing IFS, indicating longer sensing duration, can be observed. The width of the peaks varied for different IFSs with a shortest width belonging to the scaffold with highest IFS and widest peak to the lowest IFS. The width of the peaks can be related to the liquid trapping in the structure since it can elongate the evaporation or escaping of the liquid from the liquid sensor. The effect of liquid trapping on the liquid sensitivity behaviour of CNT/PLA was previously reported for two different morphologies of helical and straight line shapes (S.-z. Guo, X. Yang, M.-C. Heuzey, D. Therriault, Nanoscale 2015, 7, 6451). Increasing the duration of the liquid effect on the resistance change of the liquid sensor can be favourable for maintaining the leakage detection for a longer time.

The influence of some of structural parameters (i.e., IFS, thickness and printed patterns) on the liquid trapping is investigated and showed in FIGS. 26 to 29. The influence of IFS and scaffold thickness on their liquid sensitivity were more significant compared to the structure patterns. The values of liquid trapping indicate the amount of absorbed liquid that escaped from the scaffold structures over time.

Figure 26:
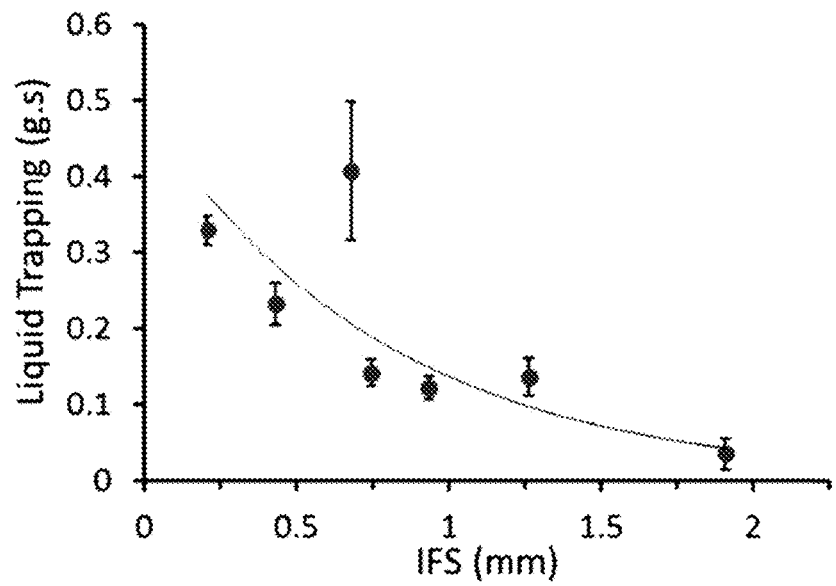
FIG. 26 shows the variation of liquid trapping during the drying time as a function of IFS.

The amount of trapped liquid is defined by the mass of liquid absorbed in the structure after the immersion and escaped the structure during the drying time which is named as liquid trapping. FIG. 26 demonstrates the amount of liquid trapping for scaffolds with different IFSs. The general trend of the IFS effect on the liquid trapping is a decrease of the amount of trapped liquid by increasing the IFS. For IFSs ranging between 0.2 to 0.68 mm, the trapping liquid value varied between 0.2 to 0.4 g·s and it decreased to 0.04 g·s by raising the IFS to 1.9 mm. This trend can be originated from the capillary forces that help to maintain higher mass of liquid for longer time before its evaporation when the pore sizes are smaller. For the scaffolds with higher IFS (e.g., 1.9 mm) due to lower capillary forces the liquid can drop and leave the structure which decreases the liquid effect during drying time.

Figure 27:
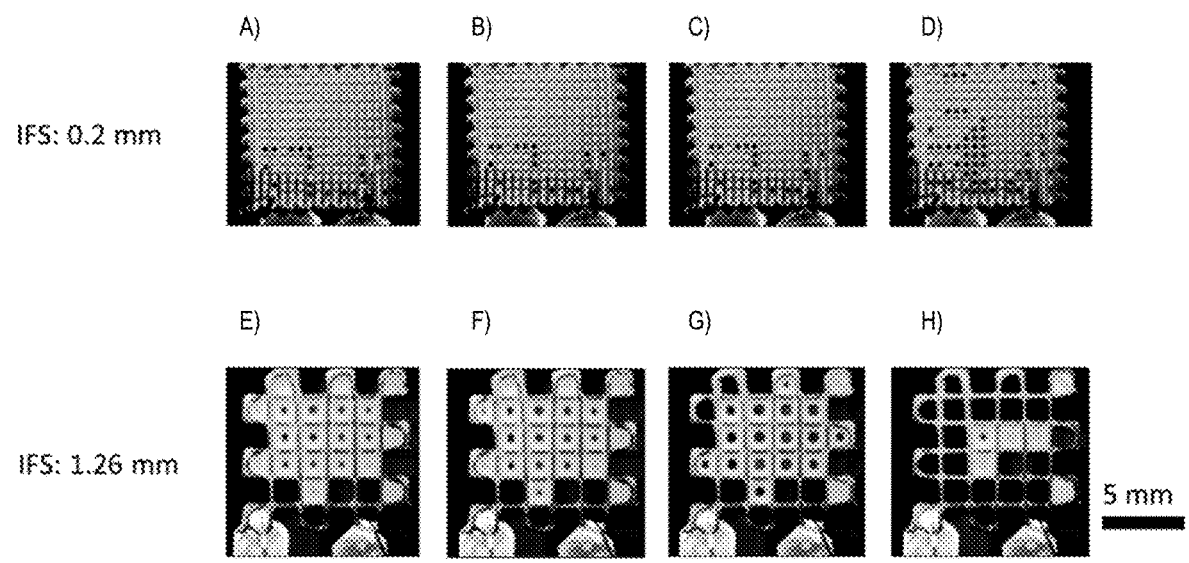
FIG. 27 A) to H) show fluorescent images of scaffolds after immersion in a fluorescent liquid, as a function of drying time—scaffold IFS 0.2 mm: A) to D) and scaffold IFS 1.26 mm: E) to H)

Optical photos of the scaffolds with two different IFS (i.e., 0.2 and 1.26 mm), placed under a UV lamp, after being immersed in a fluorescent solvent, as a function of drying time are shown in FIG. 27. No obvious change of the trapped liquid in scaffold with IFS of 0.2 mm was observed during the first 20 s of drying time while in the case of scaffold with IFS of 1.26, some portion of liquid left the structure in the same drying duration. Based on these photos after 10 minutes of drying, >70% and <30% of the liquid was remained in the scaffolds with IFS of 0.2 and 1.26 mm, respectively.

Figure 28:
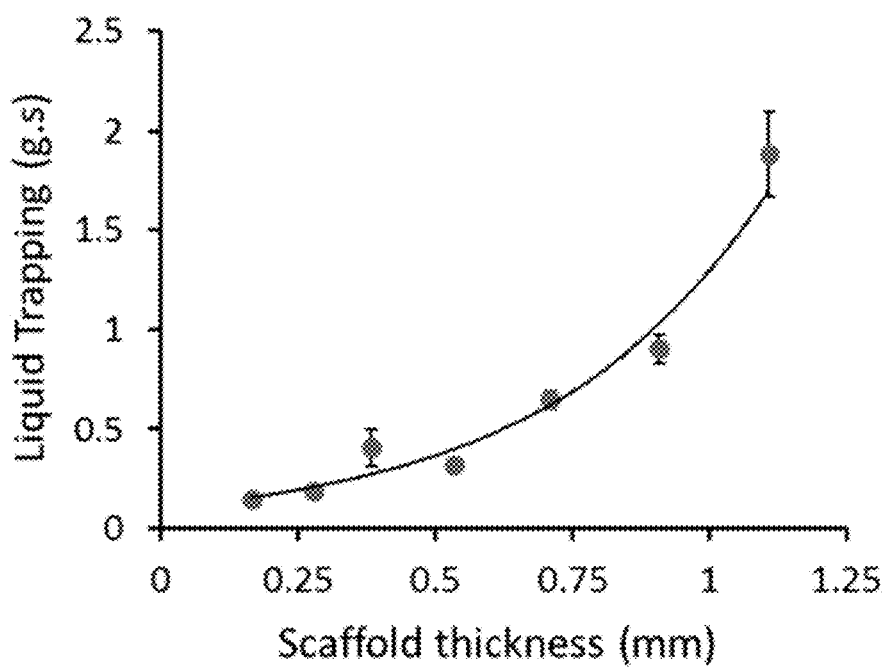
FIG. 28 is a graph of liquid trapping as a function of scaffold thickness.

The influence of scaffolds thickness on their liquid sensitivity is displayed in FIG. 28. Decreasing the scaffold thickness led to a decrease in the mass of trapped liquid. Reducing the scaffold thicknesses leads to lower vacant volume which limits the amount of trapped liquid. Higher surface to volume ratio of the trapped liquid in thinner scaffolds can also cause its faster evaporation. Scaffold printed in 10 layers with a thickness of 1.11 mm could entrap acetone for about 12 times more than two layer scaffold with a thickness of about 0.17 mm.

Figure 29:
FIG. 29 is a graph of liquid trapping as a function of structure pattern.

No significant difference in the quantity of trapped liquid was observed for scaffolds printed in different patterns with similar IFSs and number of layers (FIG. 29). These results shows that the amount of liquid entered and trapped in the structure depended more on the dimensional parameters such as IFS and thickness of scaffolds rather than the printed patterns.

2.2.3 Conductivity of the Composites

Materials with low conductivities require higher applied voltage to function as a conductive material in electrical devices. Although the conductivity of CNT/PLA with 2 wt. % of carbon nanotubes (i.e., ~45 S/m) was sufficient enough for the above investigation of the structural parameter effects on the sensitivity of the liquid sensors, inks with higher conductivities are preferred for their practical application using low applied voltages.

Thus, CNT/PLA scaffolds were printed using solvent cast 3D printing method and an ink with CNT concentrations up to 30 wt. % and electrical conductivities up to ~5100 S/m.

A comparison of the electrical conductivity of the fabricated inks to other reported polymer based conductive composites suitable for 3D printing [e.g., <100 S/m (see G. Postiglione, G. Natale, G. Griffini, M. Levi, S. Turri, Composites Part A: Applied Science and Manufacturing 2015, 76, 110), <1 S/m (see J. Czyżewski, P. Burzyński, K. Gawel, J. Meisner, Journal of Materials Processing Technology 2009, 209, 5281), and ~10 S/m (see S. J. Leigh, R. J. Bradley, C. P. Purssell, D. R. Billson, D. A. Hutchins, Plos one 2012, 7(11))] demonstrates its high conductivity.

Figure 30:
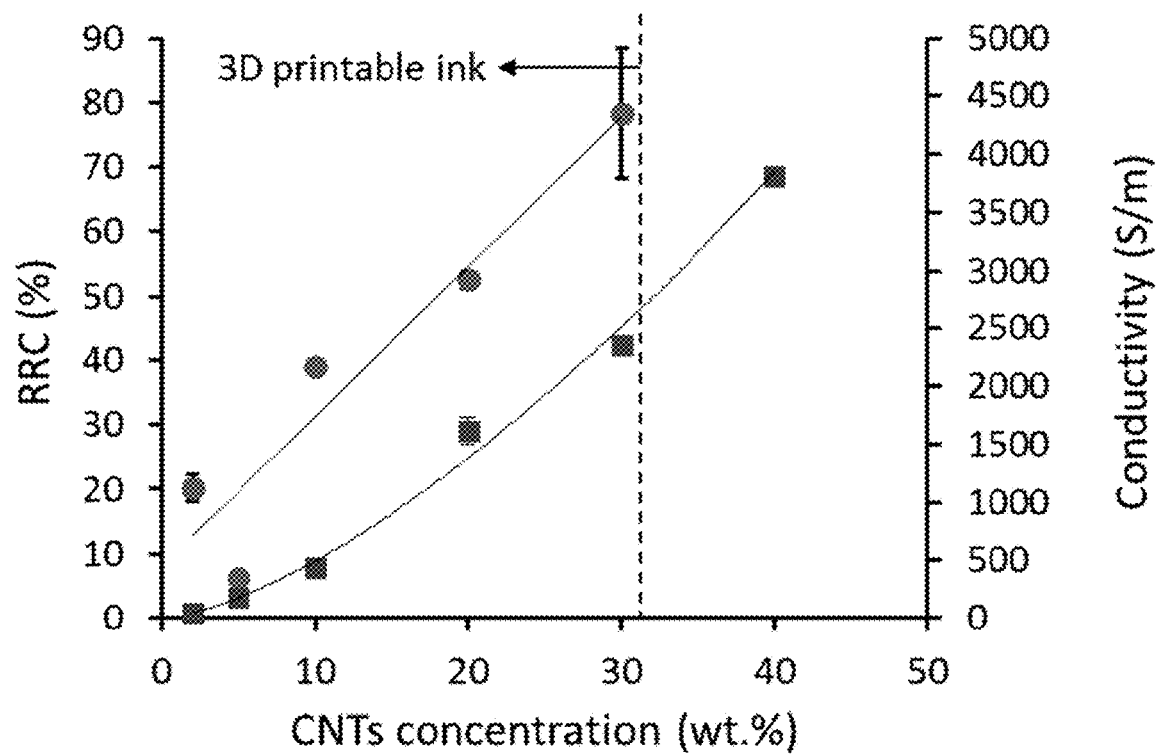
FIG. 30 shows the liquid sensitivity of CNT/PLA scaffolds (●) and electrical conductivity (■) of bulk CNT/PLA composites as a function of CNTs concentration.

SC3DP method enabled us to use CNT/PLA with high concentration of CNT since in this method the viscosity of the ink could be adjusted by varying the concentration of ink's solvent. One of the main disadvantage of materials with low conductivity for applications that requires the electrical current variation detection, is that at low applied voltages the current is extremely low that its detection is impossible. The high conductivity of the printed scaffolds allowed us to perform the liquid sensitivity tests by using an applied voltage as low as 1.5 V. The results of the liquid sensitivity tests together with the conductivity of the bulk CNT/PLA nanocomposites are shown in FIG. 30. The zone before the vertical line is the zone that the CNT/PLA ink can be used for 3D printing by SC3DP method. The liquid sensitivity tests were performed with applied voltage of 1.5 V. Higher liquid sensitivity was obtained for the liquid sensors with higher electrical conductivities.

The results showed an increasing trend of liquid sensitivity by raising the CNTs concentration in PLA. The RRC of liquid sensors could raise as high as ~78% for the scaffolds made from CNT/PLA with CNT concentration of 30 wt. %. This increase can be related to the better detection of the variation in the resistivity at low applied voltage (i.e., 1.5 V) of the CNT/PLA with higher percentages of CNTs due to their higher electrical conductivity.

2.3 Conclusions

In summary, various scaffold structures were made from CNT/PLA conductive inks using the solvent-cast 3D printing method. 3D printing enabled us to study the influence of different structural parameters (i.e., IFS, filament diameter, scaffold thickness and printing patterns) on the sensitivity of liquid sensors. The sensitivity of the liquid sensors decreased with increasing the filament diameter and/or the thickness of the fabricated scaffolds. The liquid trapping tests showed that the amount of liquid trapped in the scaffold structures increased by decreasing the IFS and/or increasing the number of printed layers.

Highly conductive CNT/PLA composite inks suitable for solvent-cast 3D printing method were fabricated by increasing the CNT concentration to 30 wt. %. The conductivity of these polymer based inks could reach up to ~5100 S/m which led to fabrication of liquid sensors that can show RRC of about 78% using low applied voltage (i.e., 1.5 V).

Example 3—Inks Based on Chitosan 3.1 Experimental Section
3.1.1 Fabrication of Nanocomposites Chitosan solutions were prepared by dissolving 4 wt % chitosan, wt % based on the total weight of the solution, (90% deacetylated, weight average molecular weight=207 kDa, from Biolog in Germany) in different aqueous solutions, i.e.:

Aqueous solution no 1: an aqueous acetic acid solution comprising 70 vol % acetic acid; and
Aqueous solution no 2: a solution of a mixture of acids in water: 70 vol % acetic acid, 10 vol % lactic acid, and 3 wt % citric acid; and
Aqueous solution no 3: aqueous solution no 1 further containing 10 wt % glycerol.

Carbon nanotubes (Nanocyl NC7000, hereinafter CNT or MWCNT) were dispersed in the chitosan solutions by ball mixing (SPEX SamplePrep 8000M Mixer/Mill). Specifically, a chitosan solution was placed inside a ball mill with the required amount of CNTs to achieve a desired CNT concentration and ball milled for 20 minutes. After mixing, composites with CNT concentrations of 5, 10, 20, 30, and 40 wt % (based on the total dry weight of the composite, i.e. the weight of chitosan+CNT) were obtained.

It should be noted that while the above refers to "solutions" of chitosan in various aqueous media, this polysaccharide in fact forms hydrogels in the above conditions.

3.1.2 Fabrication of 3D Printing Inks

After ball mixing, the above CNT/chitosan nanocomposites, with different CNT concentrations, were partially dried at room temperature with simple mixing every 15 minutes so their total CNT+chitosan concentration was about 25-30 wt % (based on the total weight of the ink), which afforded inks with appropriate viscosities for solvent-cast 3D printing (SC-3DP).

3.1.3 3D Printing of Microstructures

The above inks were loaded into a syringe (3 mL, Nordson EFD) placed inside the dispensing adaptor which was controlled by a dispensing robot (Fisnar I&J2200-4). They were extruded through a micronozzle (Nordson EFD) under an applied pressure that was controlled by a dispensing apparatus (HP-7X, Nordson EFD). CNT/chitosan scaffolds were fabricated by depositing CNT/chitosan filaments on a computer-controlled stage in a layer-by-layer manner, which was followed by the filament solidification through solvent evaporation. The applied pressure was set in range of 1.3-4.2 MPa in order to match the different inks, different micronozzles (100, 150, 200, 250, and 330 µm) were used and the robot velocity ranged from 0.4 to 10 mm/sec.

Figure 31:
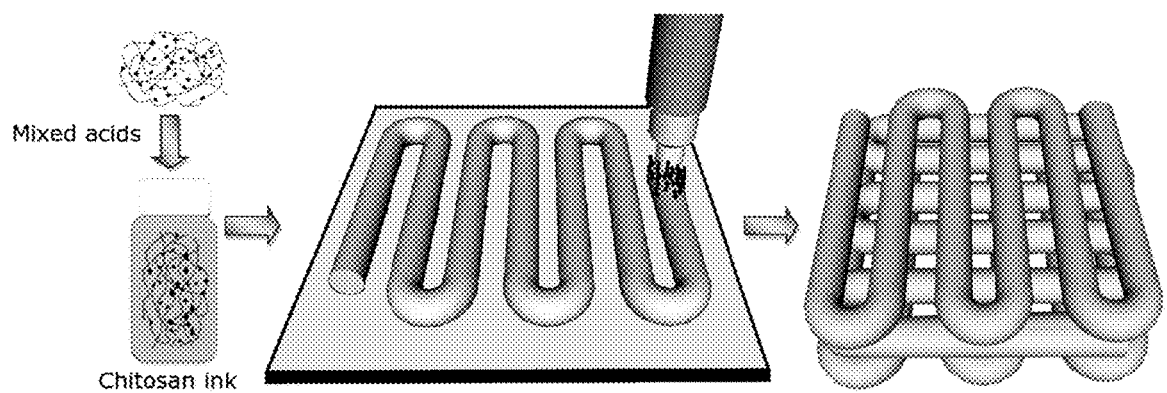
FIG. 31 illustrates the steps described in sections 3.1.1 to 3.1.3 of Example 3.

The process involved in steps 3.1.1 to 3.1.3 is illustrated in FIG. 31.

Microstructures in the shape of a spider and a starfish were produced using a CNT/chitosan ink with 10 wt % CNT under an applied pressure of 1.9 MPa and a velocity of 2 mm/sec. The files for digital 3D model of those microstructures were acquired by Thingiverse (http://www.thingiverse.com/). A software (Simplify3D) was used to generate codes from those files for 3D printing. The morphology of those microstructures were observed by optical microscopy (BX-61, Olympus).

3.1.4 Conductivity Measurements

Electrical conductivity tests were performed on filaments of CNT/chitosan composites. The above CNT/chitosan inks with different CNT concentrations were extruded through a 250 µm nozzle and a CNT/chitosan ink with 30 wt. % CNT was extruded through different micronozzles (i.e., 150, 200, 250, 330, and 410 µm) to prepare the various samples studied. The resistance of the filament produced were measured by a Keithley 6517A electrometer connected to a Keithley 8009 test fixture (Keithley Instruments, USA). The diameters of the filaments were observed by optical microscopy (BX-61, Olympus) and the lengths of the filaments were measured by a digital caliper (Lyman electronic digital caliper). The volume conductivity was then calculated from the resistance values considering the length and cross-section area of the filament samples.

3.1.5 Micro-Co-Extrusion of Chitosan

A 8 wt % chitosan solution (% based on the total weight of the solution) prepared using Aqueous solution no 2.

Figure 32:
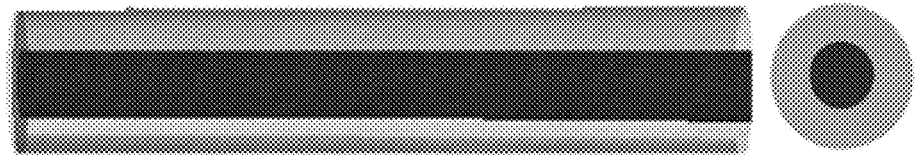
FIG. 32 shows A) a coaxial co-extruded CNT/chitosan microfilament as prepared in Example 3 viewed from the side (on the left image) and viewed axially (on the right) and B) the 3D printing (via co-extrusion) of a scaffold of coaxial CNT/chitosan microfilaments.
Figure 32:
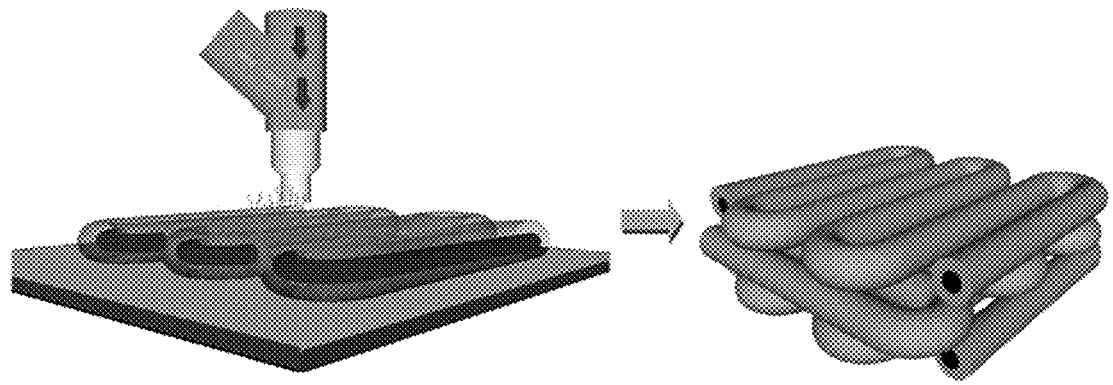

Coaxial CNT/chitosan filaments were fabricated by micro-co-extrusion. The micro-co-extrusion in a coaxial configuration involved two dispensing adaptors connected to two separate dispensing apparatuses (HP-7X, Nordson EFD). The 8 wt % chitosan solution was filled into the external syringe (3 mL, Nordson EFD) and a CNT/chitosan ink (comprising either 30 or 40 wt % CNT prepared from Aqueous solution no 2) was placed into the internal syringe. A coaxial configuration of the filaments were plotted by continuously co-extruding external and internal inks though a 838 µm nozzle with different applied pressure under a velocity ranging from 1 to 5 mm/sec at room temperature. A coaxial co-extruded CNT/chitosan microfilament and the 3D printing (via co-extrusion) of a scaffold of these coaxial CNT/chitosan microfilaments are illustrated in FIGS. 32 A) and B), respectively.

3.2 Results

Figure 33:
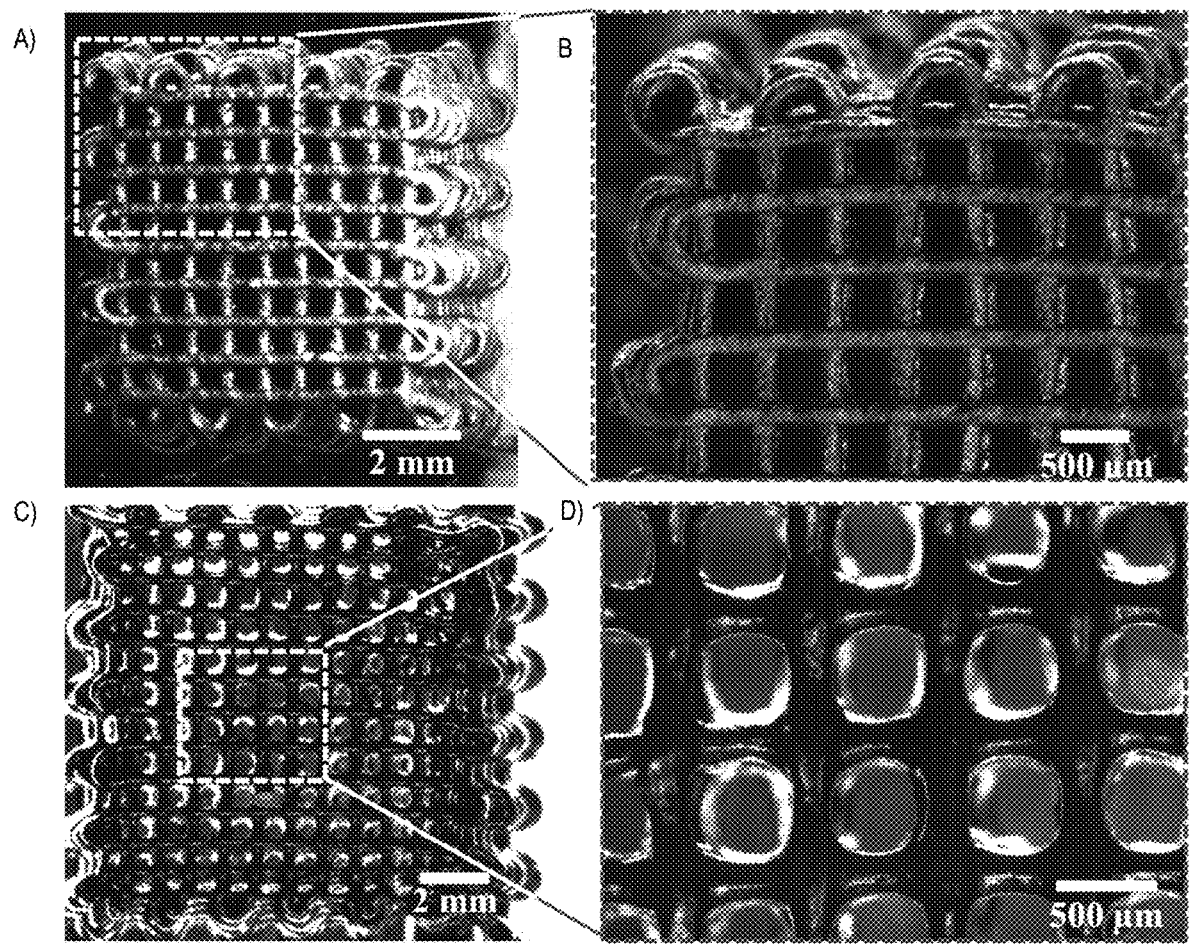
FIGS. 33 A) and B) show a scaffold comprising 30 layers printed with an ink prepared from Aqueous solution no.1 comprising 30 wt % CNT at two different magnifications; and C) and D) show a scaffold comprising 10 layers printed with an ink prepared from Aqueous solution no.2 comprising 20 wt % CNT at two different magnifications.

Examples of 3D printed scaffolds are shown in FIG. 33 A) to D). FIGS. 33 A) and B) show a scaffold comprising 30 layers printed with an ink prepared from Aqueous solution no.1 comprising 30 wt % CNT at two different magnifications. The 3D printing conditions were a pressure of 420 kPa, a velocity of 5 mm/s, and a micronozzle of 250 µm. FIGS. 33 C) and D) show a scaffold comprising 10 layers printed with an ink prepared from Aqueous solution no.2 comprising 20 wt % CNT at two different magnifications. The 3D printing conditions were a pressure of 300 kPa, a velocity of 10 mm/s, and a micronozzle of 250 µm.

Figure 34:
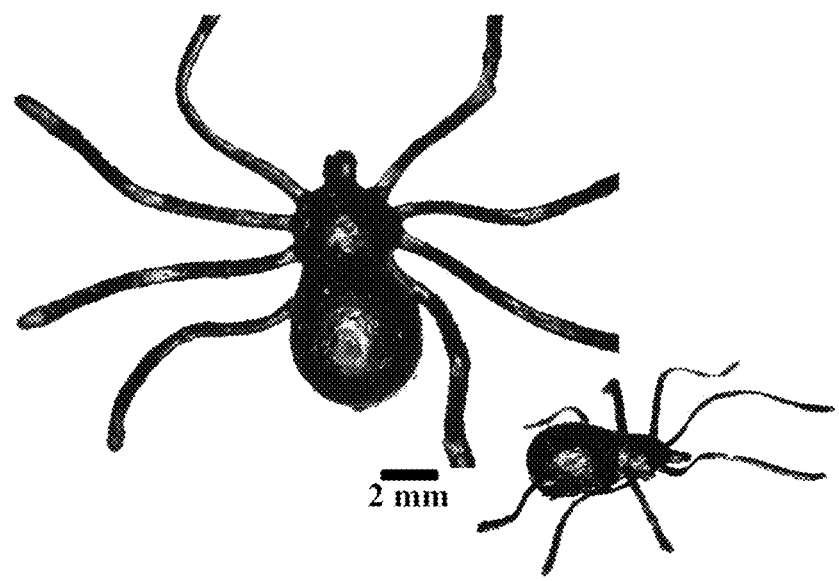
FIG. 34 shows A) a spider and B) a starfish printed using an ink prepared from Aqueous solution no.1 comprising 10 wt % CNT.
Figure 34:
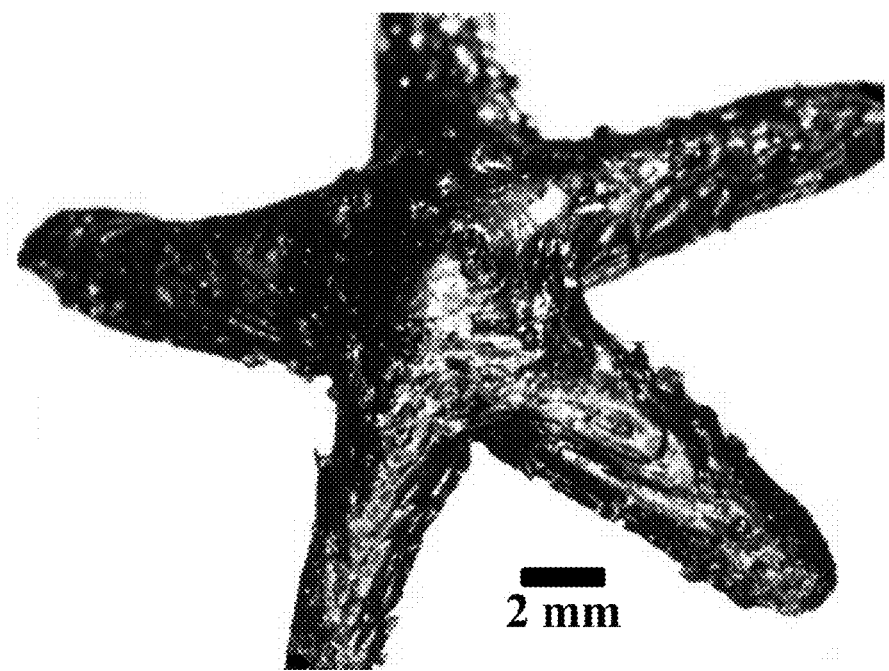

FIG. 34 shows A) a spider and B) a starfish printed with an ink prepared from Aqueous solution no.2 comprising 10 wt % CNT. The 3D printing conditions were a pressure 1.9 MPa, a velocity of 2 mm/s, and a micronozzle of 250 µm. Similar spider and starfish structures were also printed, in the same conditions, with an ink prepared from Aqueous solution no.1 comprising 10 wt % CNT. The structures printed from the ink prepared from Aqueous solution no.2 were softer and more flexible than those printed from ink prepared from Aqueous solution no.1.

Figure 35:
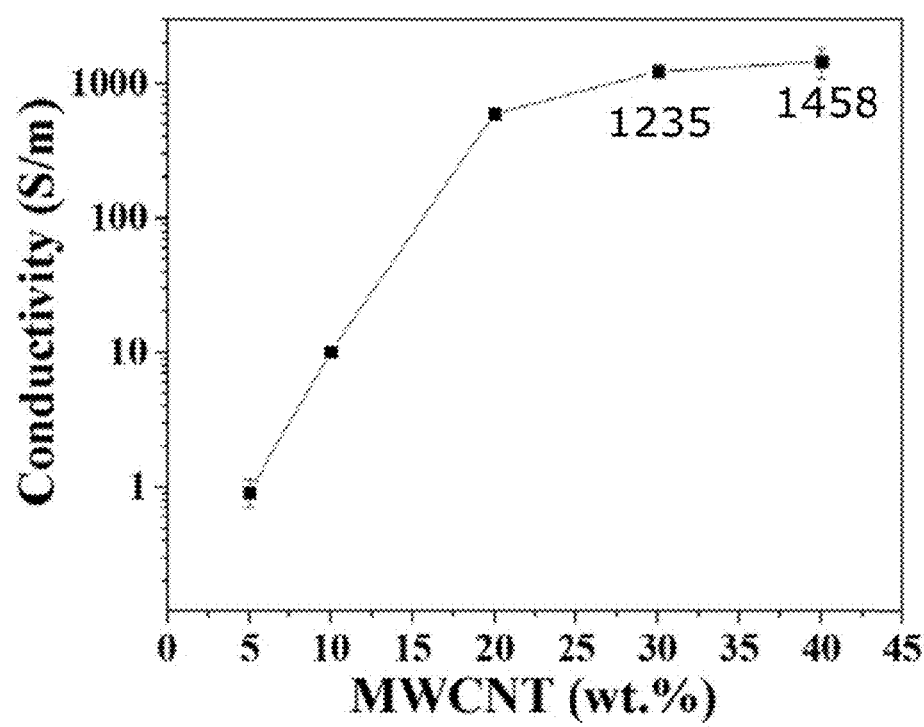
FIG. 35 shows the electrical conductivity of filaments printed from inks prepared from Aqueous solution no.1 having different CNT concentrations.
Figure 36:
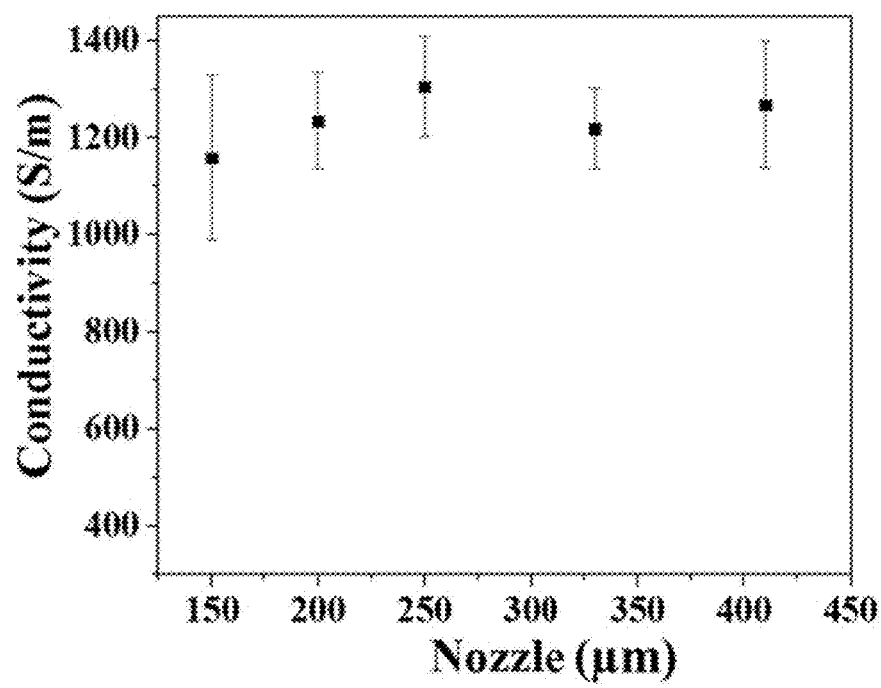
FIG. 36 shows the electrical conductivity of filaments printed from inks prepared from Aqueous solution no.1 comprising 30 wt % CNT printed with micronozzle of different sizes.
Figure 37:
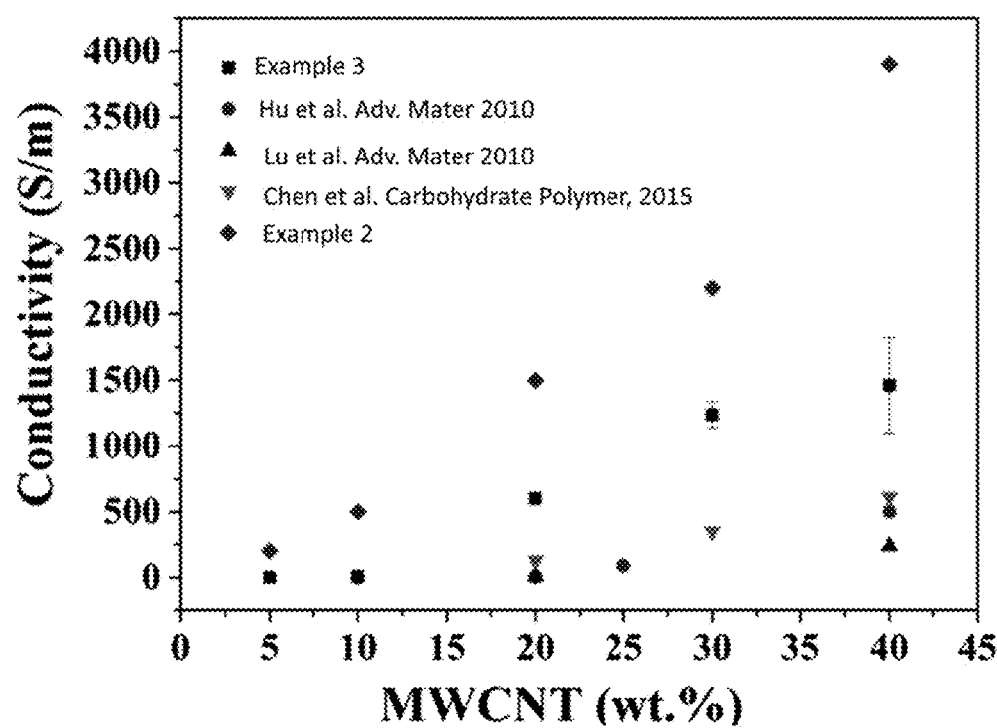
FIG. 37 compares the electrical conductivity of filaments printed from Chitosan/MWCNT inks prepared from Aqueous solution no.1 having different CNT concentrations (■); of Chitosan/SWCNT films as described in Ying Hu et al. ACS Nano, 2010 (●); of Chitosan/MWCNT films as described in Luhua Lu et al., Adv. Mater. 2010 (▲); of Chitin/MWCNT films as described in Chuchu Chen et al. Charbohydrate Polymers, 2015 (▼); and of PLA/MWCNT films prepared from inks as described in Example 2 (♦)

The filaments conductivity measurements were used to compare various inks and 3D printing conditions. FIG. 35 shows the electrical conductivity of filaments printed from inks prepared from Aqueous solution no.1 having different CNT concentrations. FIG. 36 shows the electrical conductivity of filaments printed from inks prepared from Aqueous solution no.1. comprising 30 wt % CNT printed with micronozzle of different sizes. FIG. 37 compares the electrical conductivity of filaments printed from:

- ■ Chitosan/MWCNT filament (200 µm) 3D printed from inks prepared from Aqueous solution no.1 having different CNT concentrations;
- ● Chitosan/SWCNT films described in Hu, Y.; Chen, W.; Lu, L.; Liu, J.; Chang, C., Electromechanical actuation with controllable motion based on a single-walled carbon nanotube and natural biopolymer composite. ACS nano 2010, 4 (6), 3498-3502;
- ▲ Chitosan/MWCNT films described in Lu, L.; Chen, W., Biocompatible composite actuator: a supramolecular structure consisting of the biopolymer chitosan, carbon nanotubes, and an ionic liquid. Advanced Materials 2010, 22 (33), 3745-3748;
- ▼ Chitin/MWCNT films described in Chen, C.; Yang, C.; Li, S.; Li, D., A three-dimensionally chitin nanofiber/carbon nanotube hydrogel network for foldable conductive paper. Carbohydrate polymers 2015, 134, 309-313; and
- ◆ PLA/MWCNT films prepared from the inks described in Example 2 above.

It can be seen from FIGS. 35 to 37 that the filaments produced are quite conductive and have a higher conductivity than similar composites from the above references.

Figure 38:
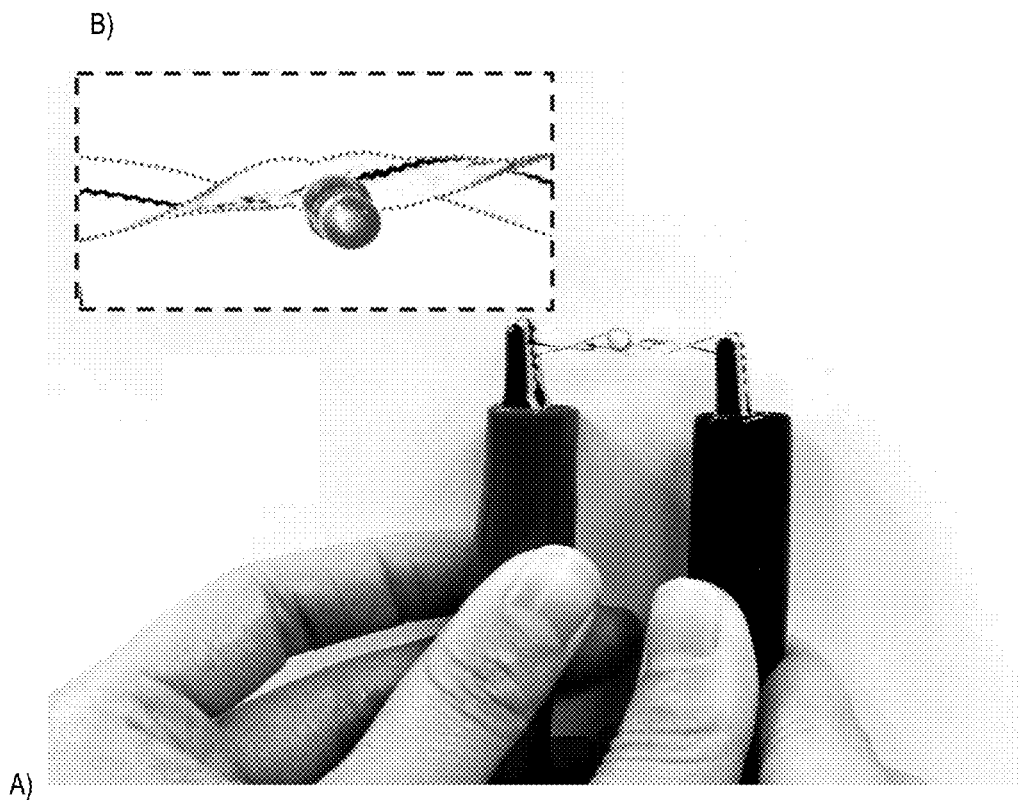
FIG. 38 A) shows a Chitosan/SWCNT filament embedded in a chitosan hydrogel film with a LED light attached to the filament, LED light is on with filament under tension, and B) shows the same, but where the LED light is off.

FIG. 38 shows a filament printed from an ink prepared from Aqueous solution no.1 having CNT concentration of 20 wt % embedded in a chitosan hydrogel film. A LED light is attached to the filament. The whole structure is flexible and stretchable. In the inset, the light is off, while it is on when put under 3V tension (main figure). For clarity, the edges of the hydrogel film are highlighted with a dash line in the inset.

Figure 39:
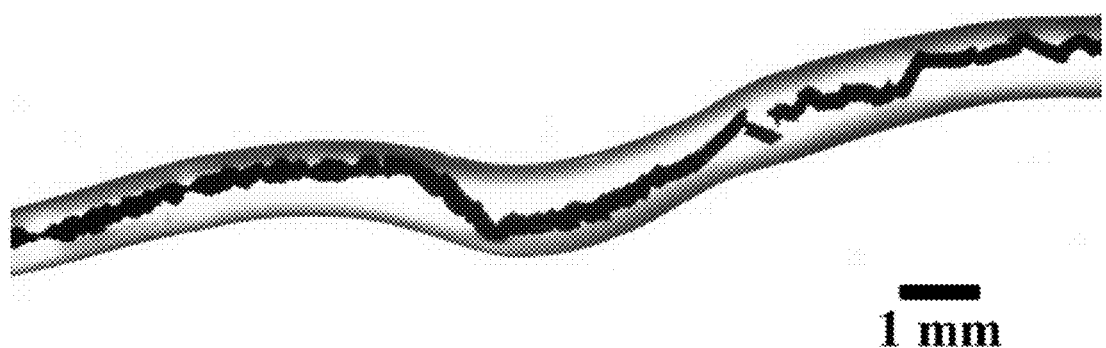
FIGS. 39 A) and B) show a coaxial co-extruded CNT/chitosan microfilament printed from the ink containing 40 wt % MWCNT at two magnifications.
Figure 39:
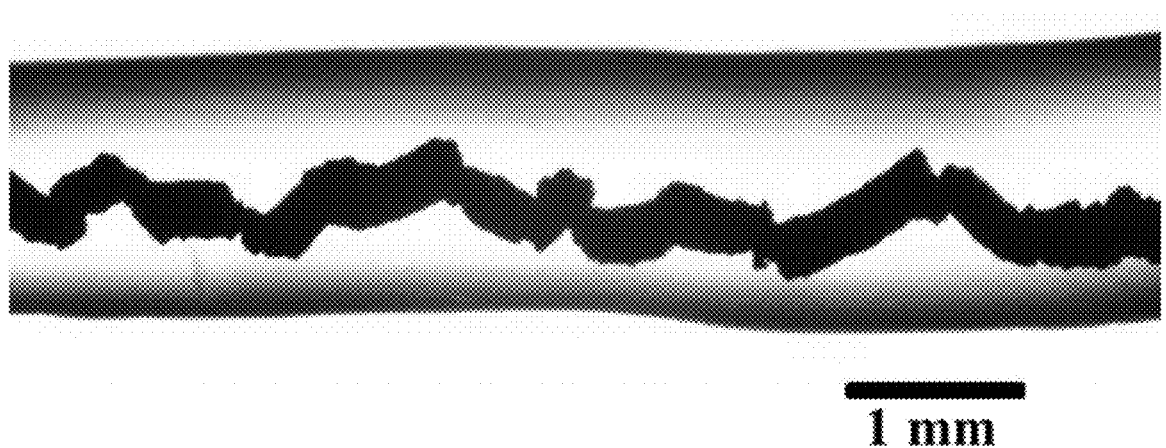
Figure 40:
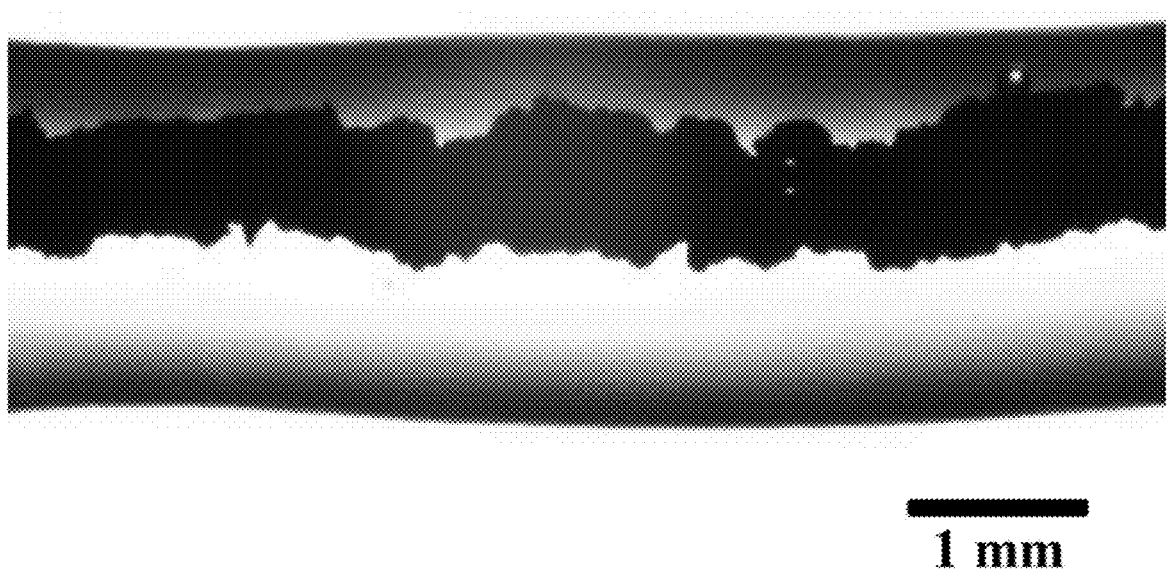
FIG. 40 shows a coaxial co-extruded CNT/chitosan microfilament printed from the ink containing 30 wt % MWCNT.

The morphology of coaxial CNT/chitosan filaments produced according to section 3.1.5 above was observed using an optical microscope (BX-61, Olympus). FIG. 39 shows a coaxial co-extruded CNT/chitosan microfilament printed from the ink containing 40 wt % MWCNT at two magnifications. FIG. 40 shows a coaxial co-extruded CNT/chitosan microfilament printed from the ink containing 30 wt % MWCNT. The microfilament prepared with a lower CNT content was more continuous.

The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:

Aldrich Materials Science, Material Matters™, Volume 11, Number 2, July 2016.
American Patent Publication no. US 2006/0078705
American Patent Publication no. US 2015/0366073
U.S. Pat. No. 4,938,816
U.S. Pat. No. 5,121,329
Chen, C.; Yang, C.; Li, S.; Li, D., A three-dimensionally chitin nanofiber/carbon nanotube hydrogel network for foldable conductive paper. Carbohydrate polymers 2015, 134, 309-313.
C. Ladd, J.-H. So, J. Muth, M. D. Dickey, Advanced Materials 2013, 25, 5081.
C. Zhu, T. Y.-J. Han, E. B. Duoss, A. M. Golobic, J. D. Kuntz, C. M. Spadaccini, M. A. Worsley, Nature communications 2015, 6.
Chinese Patent Publication no. CN 102229743A
Chinese Patent Publication no. CN 103665799A
Chinese Patent Publication no. CN104752530A
Chinese Patent no. CN101413154B
Chinese Patent no. CN102952383B
D. F. Rouhollah, M. Dubé, D. Therriault, Advanced Materials 2016, 5764.
D. J. Lipomi, M. Vosgueritchian, B. C. K. Tee, S. L. Hellstrom, J. A. Lee, C. H. Fox, Z. Bao, Nat Nano 2011, 6, 788.
D. W. Hutmacher, Biomaterials 2000, 21, 2529; D. T. Pham, R. S. Gault, International Journal of Machine Tools and Manufacture 1998, 38, 1257.
E. T. Thostenson, T. W. Chou, Advanced Materials 2006, 18, 2837;
G. Eda, M. Chhowalla, Nano Letters 2009, 9, 814;
G. Postiglione, G. Natale, G. Griffini, M. Levi, S. Turri, Composites Part A: Applied Science and Manufacturing 2015, 76, 110.
H. Zhao, J. Shen, J. Zhang, H. Wang, D. P. Wilkinson, C. E. Gu, Journal of Power Sources 2006, 159, 626. International Patent Application no. WO 2014118783 A1
J. A. Rogers, T. Someya, Y. Huang, Science 2010, 327, 1603.
J. Czyżewski, P. Burzyński, K. Gawel, J. Meisner, Journal of Materials Processing Technology 2009, 209, 5281.
J. Wang, M. Musameh, Analytical Chemistry 2003, 75, 2075; J. Wang, Electroanalysis 2005, 17, 7.

K. Chizari, D. Therriault, "Conductive Filaments from CNTs/PLA Composites", Poster presented at the ASME 2014 International Mechanical Engineering Congress and Exposition, November 14-20 2014, Montreal, Canada.

K. Chizari, D. Therriault, "Fabrication of Conductive Microfilaments and Liquid Sensor from CNTs/PLA Nanocomposites", Conference presented at the Tenth Joint Canada-Japan Workshop on Composites, August 2014, Vancouver, Canada.

K. Chizari, D. Therriault, "Fabrication of Conductive Microfilaments and Liquid Sensor from CNTs/PLA Nanocomposites" in Design, Manufacturing and Applications of Composites Tenth Workshop 2014: Proceedings of the Tenth Joint Canada-Japan Workshop on Composites, Destech Publications Inc., 2015, pp. 214-221 (proceeding of a conference held in August 2014 in Vancouver, Canada).

K. H. An, S. Y. Jeong, H. R. Hwang, Y. H. Lee, Advanced Materials 2004, 16, 1005; K. G. Ong, K. Zeng, C. A. Grimes, Sensors Journal, IEEE 2002, 2, 82.

K. Inpil, J. S. Mark, H. K. Jay, S. Vesselin, S. Donglu, Smart Materials and Structures 2006, 15, 737.

K. Kazufumi, V. Tobias, A. Timo, H. Liane, P. Petra, Smart Materials and Structures 2009, 18, 035008.

K. Kobashi, T. Villmow, T. Andres, P. Pötschke, Sensors and Actuators B: Chemical 2008, 134, 787.

L. L. Lebel, B. Aissa, M. A. E. Khakani, D. Therriault, Advanced Materials 2010, 22, 592.

Lu, L.; Chen, W., Biocompatible composite actuator: a supramolecular structure consisting of the biopolymer chitosan, carbon nanotubes, and an ionic liquid. Advanced Materials 2010, 22 (33), 3745-3748.

M. Agarwala, D. Bourell, J. Beaman, H. Marcus, J. Barlow, Rapid Prototyping Journal 1995, 1, 26.

M. Arjmand, M. Mahmoodi, G. A. Gelves, S. Park, U. Sundararaj, Carbon 2011, 49, 3430.

M. Gagné, D. Therriault, Progress in Aerospace Sciences 2014, 64, 1;

N. Hu, Y. Karube, M. Arai, T. Watanabe, C. Yan, Y. Li, Y. Liu, H. Fukunaga, Carbon 2010, 48, 680;

N. Li, Y. Huang, F. Du, X. He, X. Lin, H. Gao, Y. Ma, F. Li, Y. Chen, P. C. Eklund, Nano Letters 2006, 6, 1141;

P. F. Jacobs, Stereolithography and other RP&M technologies: from rapid prototyping to rapid tooling, Society of Manufacturing Engineers, 1995; X. Zhang, X. N. Jiang, C. Sun, Sensors and Actuators A: Physical 1999, 77, 149.

R. D. Farahani, H. Dalir, V. Le Borgne, L. A. Gautier, M. A. El Khakani, M. Lévesque, D. Therriault, Nanotechnology 2012, 23, 085502.

D. Farahani, K. Chizari, and D. Therriault, "Three-dimensional printing of helical microstructures: A review," Nanoscale, Vol. 6, pp. 10470-10485, 2014.

R. Farahani, L. Lebel, D. Therriault, Journal of Micromechanics and Microengineering 2014, 24, 055020.

R. H. Baughman, A. A. Zakhidov, W. A. de Heer, Science 2002, 297, 787.

S. Bae, H. Kim, Y. Lee, X. Xu, J.-S. Park, Y. Zheng, J. Balakrishnan, T. Lei, H. Ri Kim, Y. I. Song, Y.-J. Kim, K. S. Kim, B. Ozyilmaz, J.-H. Ahn, B. H. Hong, S. lijima, Nat Nano 2010, 5, 574;

S. J. Leigh, R. J. Bradley, C. P. Purssell, D. R. Billson, D. A. Hutchins, Plos one 2012, 7(11).

S. Stankovich, D. A. Dikin, G. H. B. Dommett, K. M. Kohlhaas, E. J. Zimney, E. A. Stach, R. D. Piner, S. T. Nguyen, R. S. Ruoff, Nature 2006, 442, 282.

S. Z. Guo, F. Gosselin, N. Guerin, A. M. Lanouette, M. C. Heuzey, D. Therriault, Small 2013, 9, 4118.

S.-Z. Guo, F. Gosselin, N. Guerin, A.-M. Lanouette, M.-C. Heuzey, D. Therriault, Small 2013, 9, 4118.

S.-Z. Guo, M.-C. Heuzey, D. Therriault, Langmuir 2014, 30, 1142.

S.-Z. Guo, X. Yang, M.-C. Heuzey, D. Therriault, Nanoscale 2015, 7, 6451.

T. Villmow, S. Pegel, A. John, R. Rentenberger, P. Pötschke, Materials Today 2011, 14, 340.

T. Yamada, Y. Hayamizu, Y. Yamamoto, Y. Yomogida, A. Izadi-Najafabadi, D. N. Futaba, K. Hata, Nat Nano 2011, 6, 296.

Hu, Y.; Chen, W.; Lu, L.; Liu, J.; Chang, C., Electromechanical actuation with controllable motion based on a single-walled carbon nanotube and natural biopolymer composite. ACS nano 2010, 4 (6), 3498-3502.

X. Kang, Z. Mai, X. Zou, P. Cai, J. Mo, Analytical Biochemistry 2007, 363, 143.

Z. Qin, B. G. Compton, J. A. Lewis, M. J. Buehler, Nat Commun 2015, 6.

The invention claimed is:

1. An ink for solvent-cast 3D printing, the ink comprising: a solution or a gel of a polymer in a volatile solvent, and carbon nanotubes dispersed in the solution or gel,
wherein the carbon nanotubes are present in a carbon nanotubes:polymer weight ratio between about 20:80 and about 40:60,
wherein the polymer and carbon nanotubes total concentration is between about 20 and about 35 wt %, based on the total weight of the ink, and
wherein the volatile solvent is a solvent that evaporates at room temperature.

2. The ink of claim 1, wherein the polymer and carbon nanotubes total concentration is between about 25 and about 30 wt %, based on the total weight of the ink.

3. The ink of claim 1, wherein the polymer is poly(lactic acid), polystyrene, poly(methyl acrylate), poly(methyl methacrylate), poly(n-butyl acrylate), poly(2-hydroxyethyl methacrylate), poly(glycidyl methacrylate), poly(acrylic acid), poly(N-N-dimethylacrylamide), poly(1-vinyl anthracene), poly(2-vinyl pyridine), poly(4-vinyl pyridine), poly (N-vinyl carbazole), poly(N-vinyl carbazole), poly(N-vinyl imidazole), poly(vinyl benzyl chloride), poly(4-vinyl benzoic acid), poly(vinyl acetate), polycaprolactone, poly(11-[4-(4-butylphenylazo)phenoxy]-undecyl methacrylate) (poly(AzoMA)), poly(ferrocenyldimethylsilane), polyisoprene, polybutadiene, polyisobutylene, poly propylene glycol, poly(ethylene glycol), a polysaccharide, or a mixture thereof.

4. The ink of claim 3, wherein the polysaccharide is chitosan.

5. The ink of claim 1, wherein the solvent is dichloromethane (DCM), chloroform ($CHCl_3$), tetrahydrofuran (THF), acetone, methanol (MeOH), ethanol (EtOH), or water.

6. The ink of claim 1, wherein the ink further comprises one or more additive.

7. The ink of claim 1, wherein the carbon nanotubes are single-wall carbon nanotubes or multiwall carbon nanotubes.

8. The ink of claim 1, wherein the polymer is poly(lactic acid) and the solvent is dichloromethane, chloroform, tetrahydrofuran, acetone, methanol, or ethanol.

9. The ink of claim 8, wherein the solvent is dichloromethane.

10. The ink of claim 1, wherein the polymer is chitosan, the solvent is water, and the solution or gel of the polymer in the volatile solvent is a chitosan hydrogel.

11. The ink of claim 10, wherein the ink further comprises one or more weak organic acid.

12. The ink of claim 11, wherein the ink comprises 70 vol % acetic acid alone or together with 10 vol % lactic acid and 3 wt % citric acid, the vol % being based on the total volume of the water and acids and the wt % being based on the total weight of the water and acids.

13. A method of manufacturing the solvent-cast 3D printing ink of claim 1, the method comprising the steps of:
   a) providing a solution or a gel of a polymer in a solvent,
   b) providing carbon nanotubes in a carbon nanotubes: polymer weight ratio of between about 20:80 and about 40:60,
   c) dispersing the carbon nanotubes in the solution or gel of the polymer by ball milling, thereby producing the ink, and
   d) avoid drying the ink, thus keeping the solvent in the ink, until the ink is used for solvent-cast 3D printing.

14. The method of claim 13, wherein the concentration of the polymer in the solution or gel of step a) is between about 2 wt % and about 15 wt %, based on the total weight of the solution or gel.

15. The method of claim 13, wherein the ball milling in step c) is carried out for 10 to 30 minutes.

16. The method of claim 13, further comprising, before or after step d), the step of adding solvent, or removing part of the solvent so that the polymer and carbon nanotubes total concentration in the ink is between about 20 and about 35 wt %, based on the total weight of the ink.

17. The method of claim 13, further comprising the step of adding one or more additives to the solvent, to the solution or gel of the polymer, or to the ink.

18. The method of claim 13, further comprising the step of packaging the ink in a 3D printer ink cartridge.

19. A method of using the solvent-cast 3D printing ink of claim 1 for manufacturing a solvent-cast 3D printed material, the method comprising the steps of:
   a) providing the solvent-cast 3D printing ink claim 1;
   b) using a 3D printer, extruding the ink through a needle into a controlled pattern; and
   c) allowing solvent evaporation, thereby providing the solvent-cast 3D printed material.

* * * * *